(12) United States Patent
Ohtsuka et al.

(10) Patent No.: US 8,699,023 B2
(45) Date of Patent: Apr. 15, 2014

(54) REFLECTIVITY MEASURING DEVICE, REFLECTIVITY MEASURING METHOD, MEMBRANE THICKNESS MEASURING DEVICE, AND MEMBRANE THICKNESS MEASURING METHOD

(75) Inventors: Kenichi Ohtsuka, Hamamatsu (JP); Tetsuhisa Nakano, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 13/822,741

(22) PCT Filed: Sep. 14, 2011

(86) PCT No.: PCT/JP2011/071020
§ 371 (c)(1),
(2), (4) Date: Mar. 13, 2013

(87) PCT Pub. No.: WO2012/036213
PCT Pub. Date: Mar. 22, 2012

(65) Prior Publication Data
US 2013/0169968 A1    Jul. 4, 2013

(30) Foreign Application Priority Data
Sep. 17, 2010   (JP) ................................. 2010-209668

(51) Int. Cl.
*G01J 3/28*        (2006.01)
(52) U.S. Cl.
USPC ........................................................ 356/326
(58) Field of Classification Search
USPC ................................. 356/326, 328
See application file for complete search history.

(56) References Cited

U.S. PATENT DOCUMENTS

| | | | |
|---|---|---|---|
| 6,504,301 B1 * | 1/2003 | Lowery | 313/512 |
| 7,251,362 B2 * | 7/2007 | Osawa et al. | 382/167 |
| 2008/0151325 A1 * | 6/2008 | Nakaya et al. | 358/474 |
| 2011/0299097 A1 | 12/2011 | Ohtsuka et al. | |
| 2012/0218561 A1 | 8/2012 | Ohtsuka et al. | |

FOREIGN PATENT DOCUMENTS

| | | |
|---|---|---|
| JP | 3-269306 | 11/1991 |
| JP | 5-322515 | 12/1993 |
| JP | 7-71924 | 3/1995 |
| JP | 7-91926 | 4/1995 |
| JP | 10-123250 | 5/1998 |
| JP | 2000-193424 | 7/2000 |
| JP | 2001-267300 | 9/2001 |
| JP | 2009-74866 | 4/2009 |

* cited by examiner

*Primary Examiner* — Tarifur Chowdhury
*Assistant Examiner* — Abdullahi Nur
(74) *Attorney, Agent, or Firm* — Drinker Biddle & Reath LLP

(57) ABSTRACT

A reflectivity measuring device 1 includes a measurement light source 30 that supplies irradiation light L1 to a measurement object, a spectroscopic detection unit 80 that detects, at multi-wavelength, intensity of the irradiation light L1 and intensity of reflected light L2 from the measurement object, a coefficient recording unit 92 that records a conversion coefficient $K(\lambda)$ for converting a detected value of each wavelength's intensity of the irradiation light L1 into a value corresponding to a detected value of each wavelength's intensity of reflected light L2 from a reference measurement object, and a reflectivity calculation unit 93 that calculates each wavelength's reflectivity based on the value corresponding to the each wavelength's intensity of the reflected light L2 from the reference measurement object obtained from the detected value of the each wavelength's intensity of the irradiation light L1 and the conversion coefficient $K(\lambda)$.

10 Claims, 22 Drawing Sheets

*Fig.6*
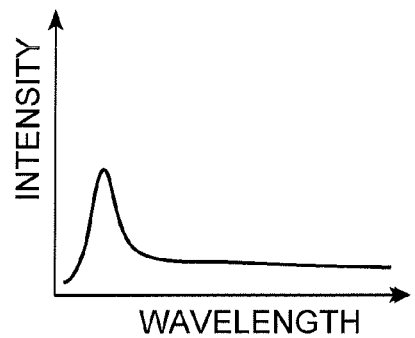
(a)
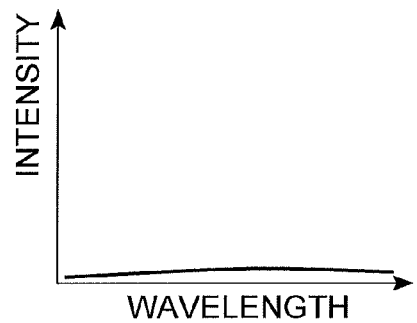
(b)
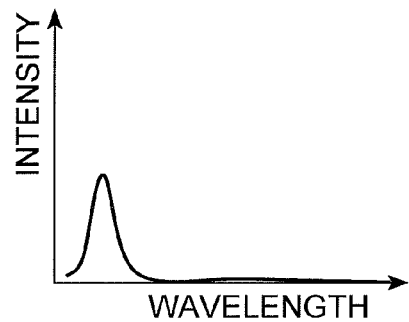
(c)
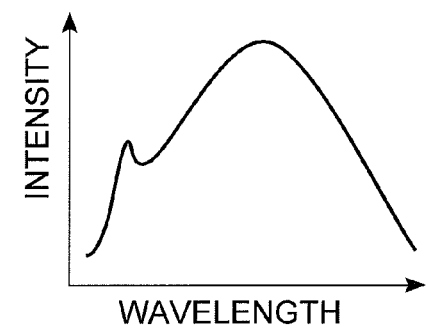
(d)
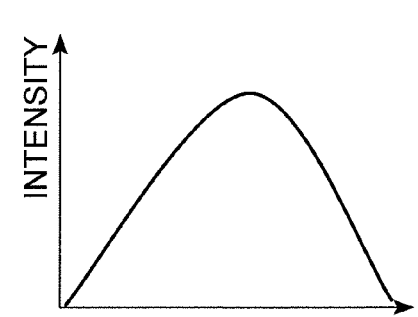
(e)

Fig.21
(a)
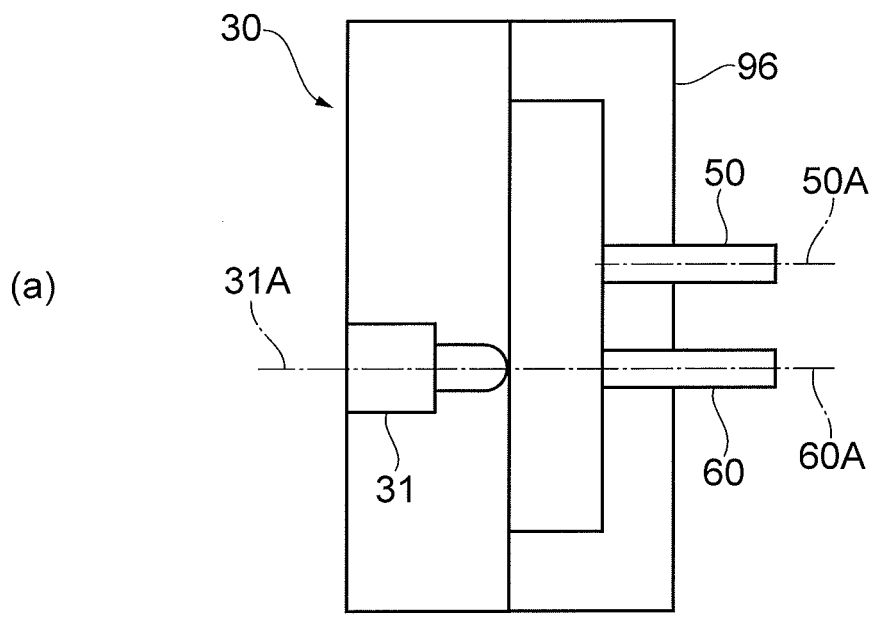
(b)
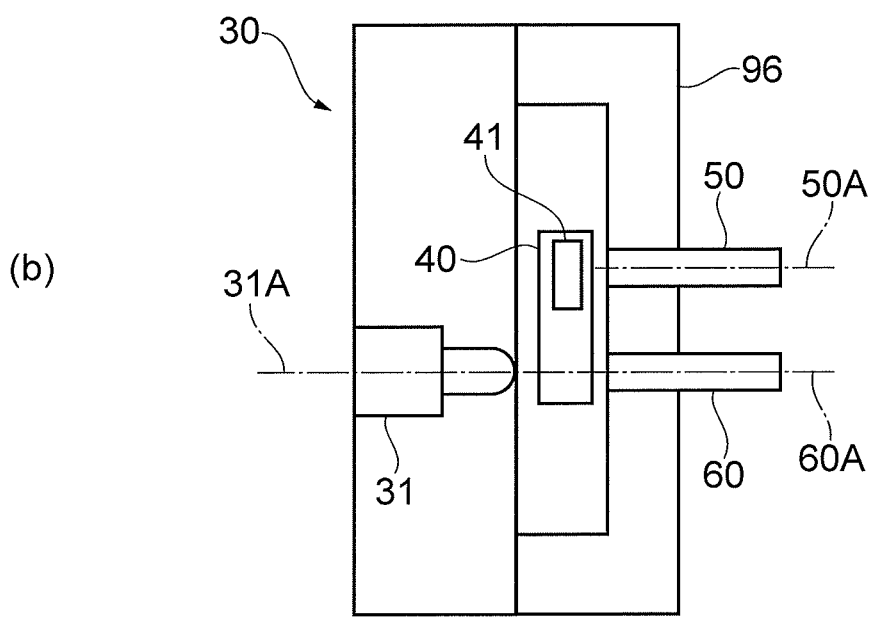

REFLECTIVITY MEASURING DEVICE, REFLECTIVITY MEASURING METHOD, MEMBRANE THICKNESS MEASURING DEVICE, AND MEMBRANE THICKNESS MEASURING METHOD

TECHNICAL FIELD

The present invention relates to a reflectivity measuring device, a reflectivity measuring method, a membrane thickness measuring device, and a membrane thickness measuring method.

BACKGROUND ART

Patent Document 1 describes a device that detects an end point of a surface treatment of a substrate for liquid crystal display. This device irradiates the liquid crystal display with light from a light source such as a xenon lamp or a halogen lamp, detects reflected light from the substrate for liquid crystal display, and detects an end point of a surface treatment from each wavelength's reflectivity of the reflected light.

Patent Document 2 describes a device that obtains the depth of etching in an etched substrate. This device irradiates the etched substrate with light from a white light source such as a xenon lamp and obtains the depth of etching in the etched substrate by detecting reflected light from the etched substrate.

CITATION LIST

Patent Literature

[Patent Document 1] Japanese Patent Application Laid-Open Publication No. H05-322515
[Patent Document 2] Japanese Patent Application Laid-Open Publication No. 2001-267300

SUMMARY OF INVENTION

Technical Problem

As a measuring method for membrane thickness of a measurement object, a method of obtaining the membrane thickness of the measurement object by detecting reflected interference light from the measurement object and calculating each wavelength's reflectivity is known. This utilizes interference due to light reflected on a front surface and a back surface of a thin membrane. An optical path becomes longer by an amount corresponding to twice the thickness of a membrane thickness for reflected light from the back surface with respect to reflected light from the front surface, and the phase changes. Interference light is obtained by interference of the reflected light from the front surface and the reflected light from the back surface. When the interference light is dispersed into multi-wavelength, there is a change in each wavelength's intensity, and the membrane thickness can be calculated from that change.

In the case where the membrane thickness is calculated from fluctuation in the each wavelength's intensity of interference light, the each wavelength's reflectivity is generally obtained in order to remove the influence of the each wavelength's intensity of light from a light source. When obtaining the each wavelength's reflectivity, it is necessary to acquire each of the each wavelength's intensity of reflected light from a reference measurement object and the each wavelength's intensity of reflected light from a measurement object. Usually, the each wavelength's intensity of the reflected light from the reference measurement object is acquired at the time of factory shipment or the like of a measuring device and recorded in a recording unit or the like of the measuring device. Then, when the membrane thickness of the measurement object is calculated, the recorded each wavelength's intensity of the reflected light from the reference measurement object is read and used.

In the device described above, fluctuation in the each wavelength's intensity of a light source used in measurement due to secular change or surrounding environment causes a difference in the intensity of irradiation light supplied to the reference measurement object from a measurement light source to acquire the each wavelength's intensity of the reflected light from the reference measurement object and the intensity of irradiation light supplied to the measurement object from the measurement light source to calculate the membrane thickness of the measurement object, and thus the each wavelength's reflectivity cannot be accurately measured.

An object of the present invention is to provide a reflectivity measuring device as well as a reflectivity measuring method that can accurately measure the each wavelength's reflectivity of a measurement object and a membrane thickness measuring device as well as a membrane thickness measuring method that can accurately measure the membrane thickness of a measurement object.

Solution to Problem

A reflectivity measuring device according to one embodiment of the present invention includes a measurement light source that supplies irradiation light to a measurement object, a spectroscopic detection unit that detects, at multi-wavelength, intensity of the irradiation light and intensity of reflected light from the measurement object, a coefficient recording unit that records a conversion coefficient for converting a detected value of each wavelength's intensity of the irradiation light into a value corresponding to each wavelength's intensity of reflected light from a reference measurement object, and a reflectivity calculation unit that calculates each wavelength's reflectivity of the measurement object based on the value corresponding to the each wavelength's intensity of the reflected light from the reference measurement object obtained from the detected value of the each wavelength's intensity of the irradiation light and the conversion coefficient.

A reflectivity measuring method according to one embodiment of the present invention includes a correction irradiation light detection step of detecting, at multi-wavelength, intensity of correction irradiation light supplied to a reference measurement object, a correction irradiation light supply step of supplying the correction irradiation light from a measurement light source to the reference measurement object, a first reflected light detection step of detecting, at multi-wavelength, intensity of reflected light of the correction irradiation light from the reference measurement object, a coefficient calculation step of calculating a conversion coefficient for converting a detected value of each wavelength's intensity of measurement irradiation light supplied to a measurement object into a value corresponding to each wavelength's intensity of reflected light of the measurement irradiation light from the reference measurement object based on a detected value of each wavelength's intensity of the correction irradiation light obtained by the correction irradiation light detection step and a detected value of each wavelength's intensity of the reflected light of the correction irradiation light obtained by the first reflected light detection step, a placement step of placing the measurement object, a measurement irradiation light detection step of detecting, at multi-wavelength, intensity of the measurement irradiation light including excitation light and fluorescence generated by the excitation light, a measurement irradiation light supply step of supplying the measurement irradiation light from the measurement light source to the measurement object, a second reflected light detection step of detecting, at multi-wavelength, intensity of reflected light of the measurement irradiation light from the measurement object, and a reflectivity calculation step of calculating each wavelength's reflectivity of the measurement object based on the value corresponding to each wavelength's intensity of the reflected light of the measurement irradiation light from the reference measurement object obtained from a detected value of a spectrum of the measurement irradiation light obtained by the measurement irradiation light detection step and the conversion coefficient and a detected value of each wavelength's intensity of the reflected light of the measurement irradiation light from the measurement object obtained by the second reflected light detection step.

With the reflectivity measuring device and the reflectivity measuring method described above, the value corresponding to the each wavelength's intensity of the reflected light from the reference measurement object can be calculated for each measurement from the detected value of the each wavelength's intensity of the irradiation light with which the measurement object is irradiated and the conversion coefficient recorded in the coefficient recording unit without using the reference measurement object upon measurement of the measurement object. Accordingly, even in the case where the each wavelength's intensity of the irradiation light fluctuates, the each wavelength's reflectivity of the measurement object can be accurately measured.

The measurement light source may be a phosphor-based white light-emitting diode that supplies irradiation light including excitation light and fluorescence generated by the excitation light. Since the life span of a light-emitting diode is longer than the life span of a halogen lamp or the like, the number of times for replacement of the measurement light source can be reduced.

The reflectivity measuring device described above may further include a reference optical waveguide having at one end a reference light reception surface irradiated with the irradiation light from the measurement light source and of which another end is optically coupled to the spectroscopic detection unit, a first measurement optical waveguide having at one end an irradiation light reception surface irradiated with the irradiation light from the measurement light source and having at another end an irradiation light supply surface that supplies the irradiation light to the measurement object, and a second measurement optical waveguide having at one end a reflected light reception surface to receive the reflected light from the measurement object and of which another end is optically coupled to the spectroscopic detection unit. With this configuration, the each wavelength's intensity of the irradiation light can be adjusted with the arrangement of the reference optical waveguide and the first measurement optical waveguide.

It may be such that the spectroscopic detection unit includes a first detection unit that detects intensity of the irradiation light at multi-wavelength and a second detection unit that detects intensity of the reflected light from the measurement object at multi-wavelength, and the other end of the reference optical waveguide is optically coupled to the first detection unit and the other end of the second measurement optical waveguide is optically coupled to the second detection unit. With such a configuration, the detection unit that detects the intensity of the irradiation light at multi-wavelength and the detection unit that detects the intensity of the reflected light from the measurement object at multi-wavelength are independent from each other. Thus, it is possible to simultaneously detect the each wavelength's intensity of the irradiation light and the each wavelength's intensity of the reflected light, and the each wavelength's reflectivity of the measurement object can be accurately measured. Further, time required for measurement of the each wavelength's reflectivity can be shortened.

It may be such that optical waveguide selecting device for causing the irradiation light from the measurement light source to be selectively incident upon one of the reference light reception surface and the irradiation light reception surface is further included, the spectroscopic detection unit includes a third detection unit that detects intensity of the irradiation light at multi-wavelength and detects intensity of the reflected light at multi-wavelength, and the other end of the reference optical waveguide and the other end of the second measurement optical waveguide are optically coupled to the third detection unit. With such a configuration, it is possible to configure the spectroscopic detection unit with one detection unit, and the reflectivity measuring device can be manufactured with a simple configuration.

The light amount of the irradiation light with which the irradiation light reception surface is irradiated may be larger than the light amount of the irradiation light with which the reference light reception surface is irradiated. Thus, even in the case where the irradiation light or the reflected light has attenuated due to passing through the optical waveguide or the like, the light amount necessary for accurately measuring the each wavelength's reflectivity can be ensured. Also, the first measurement optical waveguide may be arranged such that the irradiation light reception surface and the measurement light source are opposed. With such an arrangement, it is possible to increase the light amount of the irradiation light with which the first measurement optical waveguide is irradiated.

The first measurement optical waveguide and the reference optical waveguide may be arranged such that a central axis of the first measurement optical waveguide and a central axis of the reference optical waveguide are line symmetrical with respect to an axis passing through the measurement light source. In the case where light having directionality as in light from a light-emitting diode is used as the irradiation light, for example, a detected value of the each wavelength's intensity of the irradiation light that enters the optical waveguide can differ depending on the positional relationship of the measurement light source and the optical waveguide. With the above-described configuration, the difference of a detected value of the each wavelength's intensity of the irradiation light with which the reference optical waveguide is irradiated and a detected value of the each wavelength's intensity of the irradiation light with which the first measurement optical waveguide is irradiated can be reduced, and the each wavelength's reflectivity can be accurately measured.

Further, a membrane thickness measuring device includes the reflectivity measuring device described above. Also, in a membrane thickness measuring method, the reflectivity measuring method described above is included, and membrane thickness of the measurement object is calculated based on the each wavelength's reflectivity obtained through the reflectivity measuring method. Accordingly, it is possible to accurately calculate the each wavelength's reflectivity of a measurement object necessary for measurement of membrane thickness, and the membrane thickness of the measurement object can be accurately measured.

Advantageous Effects of Invention

With the reflectivity measuring device and the reflectivity measuring method according to the present invention, the each wavelength's reflectivity of a measurement object can be accurately measured. Also, with the membrane thickness measuring device and the membrane thickness measuring method according to the present invention, the membrane thickness of a measurement object can be accurately measured.

BRIEF DESCRIPTION OF DRAWINGS

FIG. 6(a) is a graph showing the each wavelength's intensity of a dark signal. FIG. 6(b) is a graph showing the each wavelength's intensity of a dark current component included in the dark signal. FIG. 6(c) is a graph showing the each wavelength's intensity of a signal caused by ambient light included in the dark signal. FIG. 6(d) is a graph showing the each wavelength's intensity of irradiation light including the dark signal. FIG. 6(e) is a graph showing the each wavelength's intensity of the irradiation light after dark subtraction correction has been performed.

FIG. 21(a) is a configuration diagram showing still another modified example of the configuration of the measurement light source, the reference optical waveguide, and the first measurement optical waveguide. FIG. 21(b) is a configuration diagram showing still another modified example of the configuration of the measurement light source, the reference optical waveguide, and the first measurement optical waveguide.

DESCRIPTION OF EMBODIMENTS

Embodiments for a reflectivity measuring device and a reflectivity measuring method according to the present invention will be described below in detail with reference to the accompanying drawings. Note that, in the description of the drawings, the same components are denoted by the same reference signs, and redundant descriptions are omitted.

First Embodiment

Figure 1:
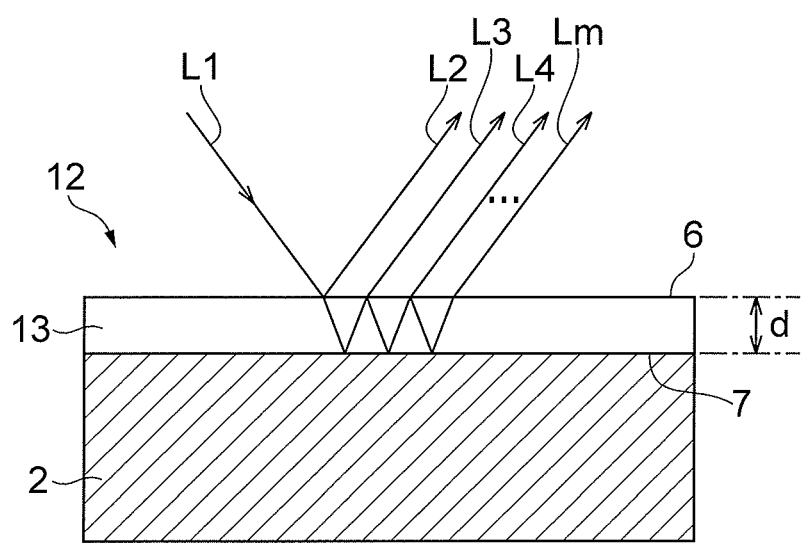
FIG. 1 is a view schematically showing a measuring method for the membrane thickness of a measurement object.

First, the principle of membrane thickness measurement utilizing interference due to reflected light will be described. In an example shown in FIG. 1, a semiconductor membrane 13 formed on a substrate 2 is shown as one example of a membrane-shaped measurement object. For a membrane thickness d thereof, irradiation light L1 for membrane thickness measurement is supplied with respect to a sample 12 formed of the substrate 2 and the semiconductor membrane 13 from an upper surface 6 (first surface) side of the semiconductor membrane 13 that is an opposite side of the substrate 2. Then, by detecting interference light generated through interference of reflected light L2 from the upper surface 6 and reflected light L3 to Lm from a lower surface 7 (second surface that is a boundary surface of the substrate 2 and the semiconductor membrane 13), the membrane thickness d of the semiconductor membrane 13 is calculated.

Figure 2:
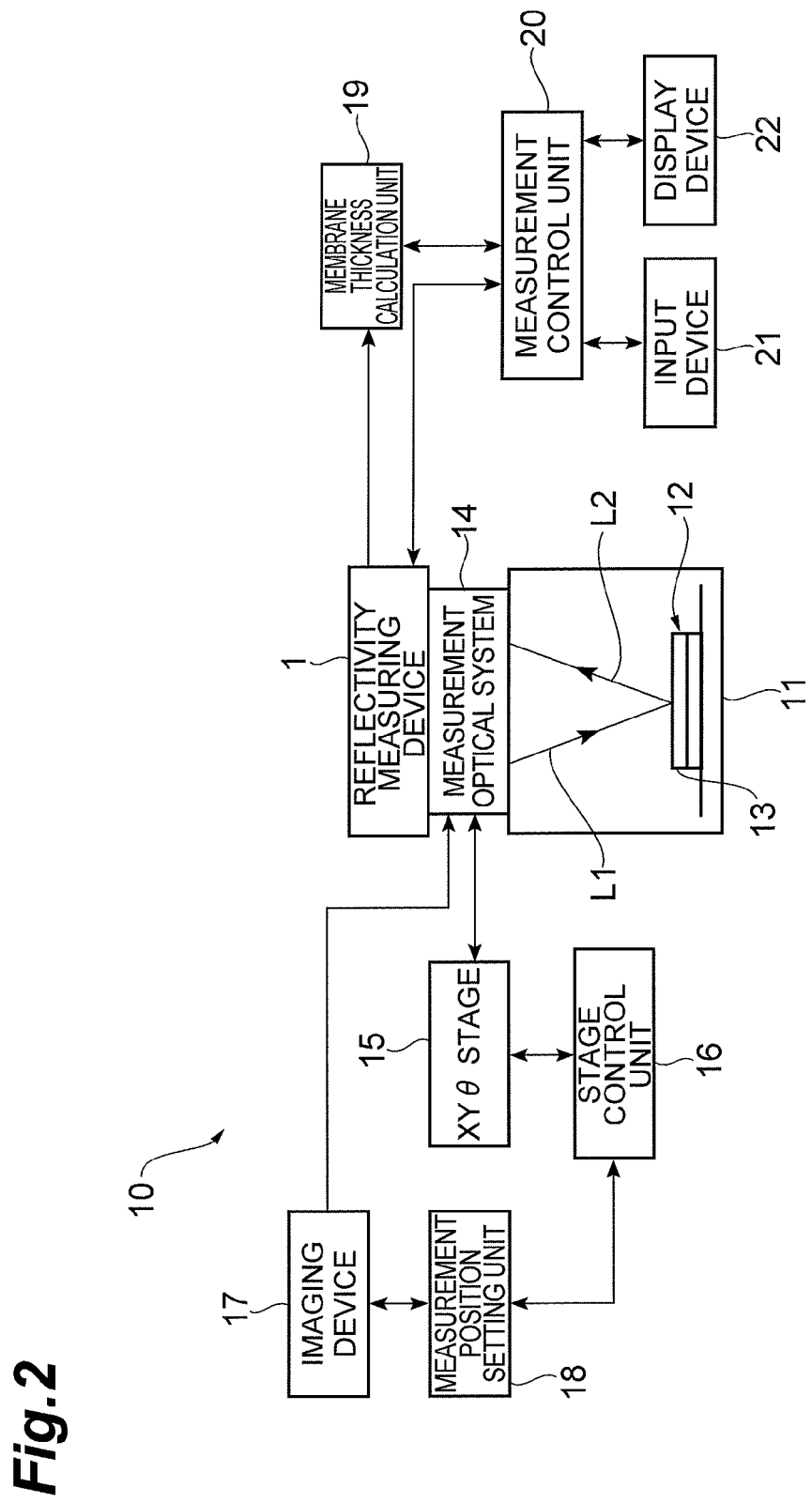
FIG. 2 is a block diagram showing the configuration of a membrane thickness measuring device.

Next, the configuration of a membrane thickness measuring device including a reflectivity measuring device according to this embodiment will be described. FIG. 2 is a block diagram showing the configuration of one embodiment for a membrane thickness measuring device 10. In FIG. 2, an example in which the semiconductor membrane 13 of the sample 12 placed in a process chamber of a sample measurement unit 11 is the measurement object is shown. The membrane thickness measuring device 10 includes a reflectivity measuring device 1, a measurement optical system 14, and a membrane thickness calculation unit 19 described later.

The membrane thickness calculation unit 19 is membrane thickness calculating device for calculating the membrane thickness of the semiconductor membrane 13 that is the measurement object, and calculates the membrane thickness based on a calculated value of each wavelength's reflectivity (hereinafter, "each wavelength's reflectivity" is referred to as "spectroscopic reflectivity data") output from the reflectivity measuring device 1. An input terminal of the membrane thickness calculation unit 19 is connected to an output terminal of the reflectivity measuring device 1. Note that the membrane thickness calculation unit 19 may be configured by a computer in which a predetermined calculation program is executed, for example.

To the membrane thickness calculation unit 19, a measurement control unit 20 is connected. The measurement control unit 20 references membrane thickness information or the like output from the membrane thickness calculation unit 19 and performs necessary control for an operation such as a membrane thickness measurement operation in the membrane thickness measuring device 10 by controlling respective device parts of the membrane thickness measuring device 10 such as the reflectivity measuring device 1.

To the measurement control unit 20, an input device 21 and a display device 22 are connected. The input device 21 is used for input by an operator of information, condition, instruction, or the like necessary for the measurement operation in the reflectivity measuring device 1 and the membrane thickness measuring device 10. The display device 22 is used for display for the operator of necessary information about the measurement operation described above.

The measurement optical system 14 irradiates a predetermined measurement position of the sample 12 with the irradiation light L1 supplied from the reflectivity measuring device 1 and guides the reflected light L2 reflected on the surface of the sample 12 to the reflectivity measuring device 1. With respect to the measurement optical system 14, a first measurement optical waveguide (described later and therefore not shown) that guides the irradiation light L1 from the reflectivity measuring device 1 and a second measurement optical waveguide (described later and therefore not shown) that guides the reflected light L2 from the sample 12 described later to the reflectivity measuring device 1 are optically coupled. The measurement optical system 14 is provided with the sample measurement unit 11 inside which the sample 12 that is the measurement object is placed. For the measurement object, there are a reference measurement object in which the each wavelength's reflectivity is known and a measurement object that is an object of membrane thickness measurement.

The measurement optical system 14 is provided with an XYθ stage 15. The XYθ stage 15 adjusts the measurement position and the measurement condition for the membrane thickness of the semiconductor membrane 13 in the membrane thickness measuring device 10 by adjusting the position, angle, or the like of the measurement optical system 14 in an X-direction, Y-direction, or θ-direction. The XYθ stage 15 is driven and controlled by a stage control unit 16.

The sample 12 in the sample measurement unit 11 and the measurement optical system 14 are further provided with an imaging device 17 and a measurement position setting unit 18. The imaging device 17 is a position-check imaging device for checking the measurement position of the membrane thickness of the semiconductor membrane 13 in the membrane thickness measuring device 10. The measurement position setting unit 18 references an image of the sample 12 including the semiconductor membrane 13 acquired by the imaging device 17 via the measurement optical system 14 and sets the membrane thickness measurement position with respect to the sample 12.

Figure 3:
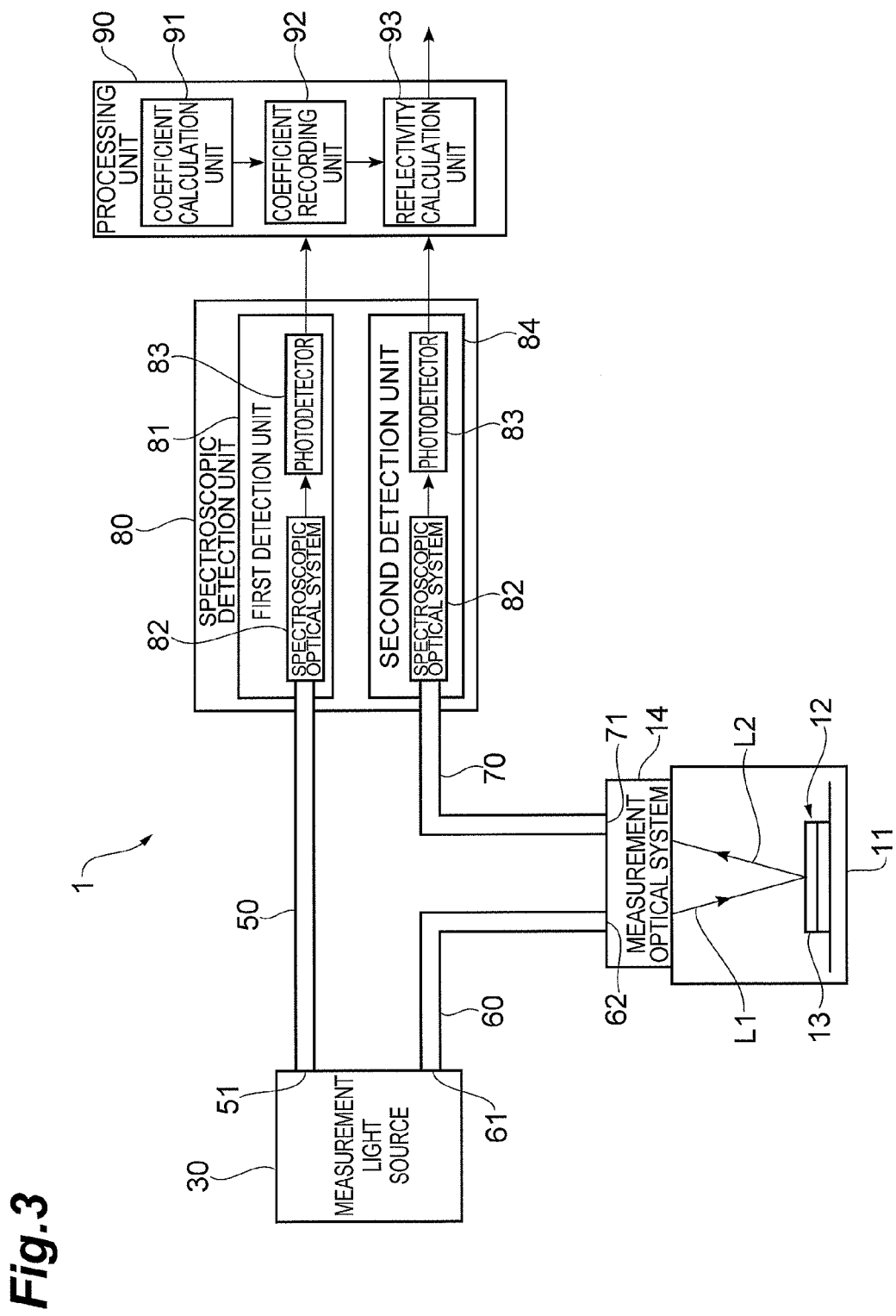
FIG. 3 is a block diagram showing the configuration of a first embodiment for a reflectivity measuring device.

Next, the configuration of the reflectivity measuring device 1 according to the first embodiment will be described. FIG. 3 shows one example of the configuration of the reflectivity measuring device 1 according to the first embodiment. The reflectivity measuring device 1 is configured to include a measurement light source 30, a reference optical waveguide 50, a first measurement optical waveguide 60, a second measurement optical waveguide 70, a spectroscopic detection unit 80, and a processing unit 90.

The reflectivity measuring device 1 is provided with the measurement light source 30 that supplies the irradiation light L1 with respect to the semiconductor membrane 13 of the sample 12 in the sample measurement unit 11 via the measurement optical system 14. The measurement light source 30 supplies the irradiation light L1 including at least a wavelength component over a predetermined band to the semiconductor membrane 13 that is the measurement object. For the measurement light source 30, a phosphor-based white light-emitting diode (hereinafter referred to as "phosphor-based white LED") that causes irradiation of light including excitation light and fluorescence generated by the excitation light may be suitably used, for example. The white LED generates fluorescence of a long-wavelength region through irradiation of excitation light of a short wavelength to phosphor and produces white light through mixture of the excitation light and the fluorescence. Note that, as the measurement light source 30, a light source such as a xenon lamp or a halogen lamp or a tri-color LED-based white LED in which a red LED, a green LED, and a blue LED are combined may also be used.

The first measurement optical waveguide 60 guides the irradiation light L1 from the measurement light source 30 to the measurement optical system 14. The first measurement optical waveguide 60 has an irradiation light reception surface 61 that is irradiated with the irradiation light L1 from the measurement light source 30 and an irradiation light supply surface 62 that supplies the irradiation light L1 to the measurement object. The irradiation light reception surface 61 is optically coupled to the measurement light source 30, and the irradiation light supply surface 62 is optically coupled to the measurement optical system 14. As the first measurement optical waveguide 60, an optical fiber may be suitably used, for example.

The second measurement optical waveguide 70 guides the reflected light L2 from the sample 12 to the reflectivity measuring device 1 via the measurement optical system 14. The second measurement optical waveguide 70 has a reflected light reception surface 71 that receives the reflected light L2 from the sample 12. The reflected light reception surface 71 is optically coupled to the measurement optical system 14. The other end of the second measurement optical waveguide 70 is optically coupled to the spectroscopic detection unit 80. As the second measurement optical waveguide 70, an optical fiber may be suitably used, for example.

One end of the reference optical waveguide 50 is provided with a reference light reception surface 51 that is irradiated with the irradiation light L1 from the measurement light source 30. The reference light reception surface 51 is optically coupled to the measurement light source 30. The other end of the reference optical waveguide 50 is optically coupled to the spectroscopic detection unit 80. As the reference optical waveguide 50, an optical fiber may be suitably used, for example.

The spectroscopic detection unit 80 is configured to include a first detection unit 81 that detects the intensity of the irradiation light L1 at multi-wavelength and acquires a detected value of each wavelength's intensity (hereinafter, "detected value of each wavelength's intensity" is referred to as "spectrum waveform") and a second detection unit 84 that acquires the spectrum waveform of the reflected light L2. The first detection unit 81 is configured to include a spectroscopic optical system 82 and a photodetector 83. The spectroscopic optical system 82 disperses light that has entered the spectroscopic optical system 82 into multi-wavelength and outputs the light dispersed into wavelengths to the photodetector 83. The photodetector 83 acquires the spectrum waveform of the light output from the spectroscopic optical system 82 and outputs the acquired spectrum waveform to the processing unit 90. To an input terminal of the spectroscopic optical system 82 of the first detection unit 81, the other end of the reference optical waveguide 50 is optically coupled. An output terminal of the photodetector 83 is connected to an input terminal of the processing unit 90. Also, the second detection unit 84 is configured to include the spectroscopic optical system 82 and the photodetector 83 in a similar manner to the first detection unit 81. To an input terminal of the spectroscopic optical system 82 of the second detection unit 84, the other end of the second measurement optical waveguide 70 is optically coupled. An output terminal of the photodetector 83 is connected to another input terminal of the processing unit 90.

The processing unit 90 is configured to include a coefficient calculation unit 91, a coefficient recording unit 92, and a reflectivity calculation unit 93. The coefficient calculation unit 91 calculates a conversion coefficient for converting the spectrum waveform of the irradiation light L1 to a value corresponding to the spectrum waveform of the reflected light L2 from the reference measurement object. The coefficient recording unit 92 records the calculated conversion coefficient. The reflectivity calculation unit 93 calculates the spectroscopic reflectivity data of the measurement object. The input terminal of the processing unit 90 is connected to the output terminal of the photodetector 83 of the first detection unit 81. Another input terminal of the processing unit 90 is connected to the output terminal of the photodetector 83 of the second detection unit 84. An output terminal of the processing unit 90 is connected to the input terminal of the membrane thickness calculation unit 19 shown in FIG. 2.

The coefficient calculation unit 91 calculates the conversion coefficient based on the spectrum waveform of the irradiation light L1 with which the reference measurement object is irradiated and the spectrum waveform of the reflected light L2 from the reference measurement object. The coefficient calculation unit 91 outputs the calculated conversion coefficient to the coefficient recording unit 92. An output terminal of the coefficient calculation unit 91 is connected to an input terminal of the coefficient recording unit 92. The coefficient calculation unit 91 may be configured by a computer in which a predetermined calculation program is executed, for example.

The coefficient recording unit 92 records the conversion coefficient described above and outputs the conversion coefficient to the reflectivity calculation unit 93. The input terminal of the coefficient recording unit 92 is connected to the output terminal of the coefficient calculation unit 91.

The reflectivity calculation unit 93 calculates the spectroscopic reflectivity data of the measurement object based on the spectrum waveform of the reflected light L2 from the measurement object and the value corresponding to the spectrum waveform of the reflected light L2 from the reference measurement object. The value is obtained from the spectrum waveform of the irradiation light L1 with which the measurement object is irradiated and the conversion coefficient. The reflectivity calculation unit 93 outputs the calculated spectrum waveform to the membrane thickness calculation unit 19 (see FIG. 2). An output terminal of the reflectivity calculation unit 93 is connected to the input terminal of the membrane thickness calculation unit 19 (see FIG. 2). The reflectivity calculation unit 93 may be configured by a computer in which a predetermined calculation program is executed, for example.

Figure 4:
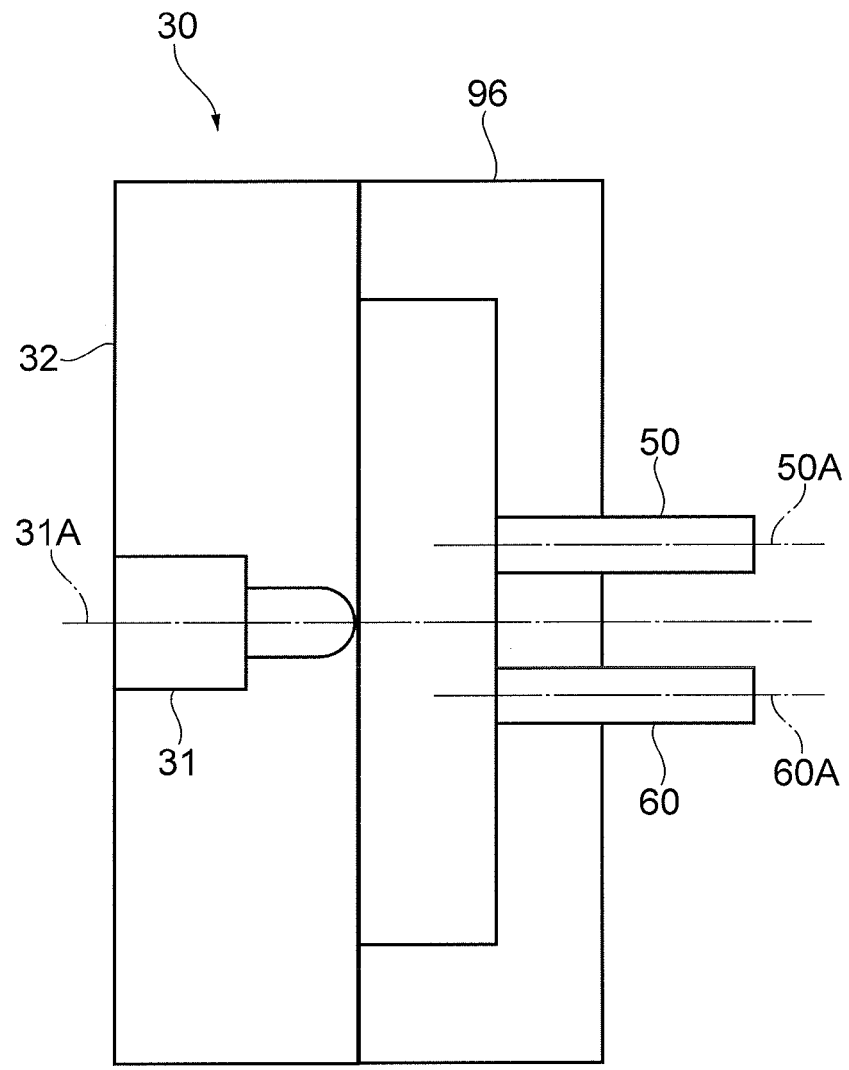
FIG. 4 is a configuration diagram showing one example of the configuration of a measurement light source, a reference optical waveguide, and a first measurement optical waveguide.

FIG. 4 shows the configuration of the measurement light source 30, the reference optical waveguide 50, and the first measurement optical waveguide 60 according to this embodiment. The measurement light source 30 is configured to include a phosphor-based white LED 31 and a light source main unit 32. The reference optical waveguide 50 and the first measurement optical waveguide 60 are held by an optical waveguide holding unit 96. In this embodiment, the reference optical waveguide 50 and the first measurement optical waveguide 60 are arranged such that a central axis 50A of the reference optical waveguide 50 and a central axis 60A of the first measurement optical waveguide 60 are line symmetrical with respect to an axis 31A passing through the white LED 31.

Figure 5:
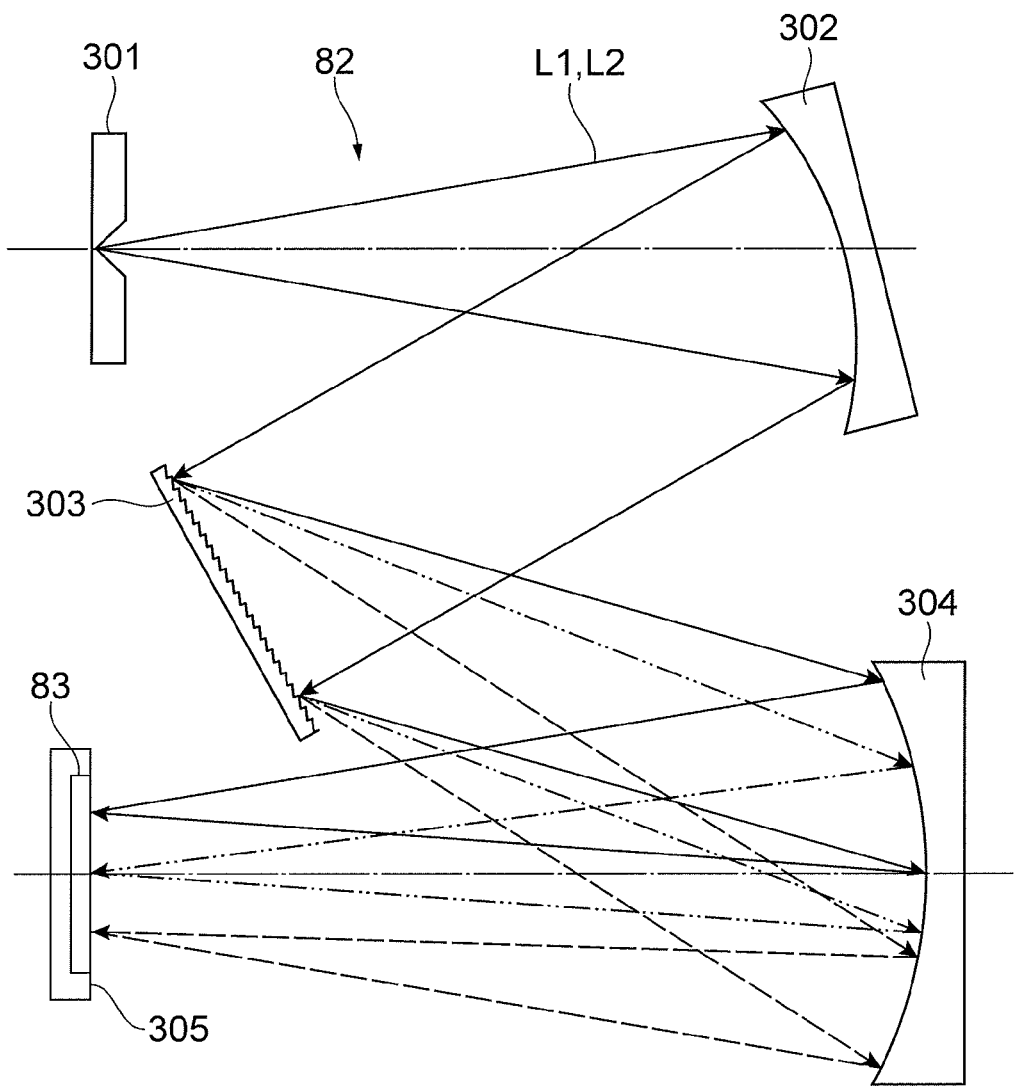
FIG. 5 is a view showing one example of the configuration of a spectroscopic optical system.

FIG. 5 shows one example of the configuration of the spectroscopic optical system 82. Specifically, the spectroscopic optical system 82 disperses the irradiation light L1 and the reflected light L2 of the irradiation light L1 from the measurement object to be detectable at multi-wavelength. The spectroscopic optical system 82 is configured to include an entrance slit 301, a collimating optical system 302, a diffraction grating 303 that is a dispersion element, and a focusing optical system 304. With this configuration, light dispersed into wavelengths with the diffraction grating 303 forms an image of each wavelength's component on an output surface 305 of the wavelength spectrum via the focusing optical system 304 and is detected at multi-wavelength by the photodetector 83 arranged on the output surface 305. Note that, unlike this example, the spectroscopic optical system 82 that disperses the irradiation light L1 and the reflected light L2 from the measurement object so as to be detectable at multi-wavelength can be suitably configured by using a band-pass filter, for example.

As shown in FIG. 5, the photodetector 83 is provided as detecting device for detecting the intensity of wavelength components with respect to the light dispersed into multi-wavelength components by the spectroscopic optical system 82. Specifically, the photodetector 83 detects the intensity of output light dispersed by the spectroscopic optical system 82 at wavelength components in units of several nanometers. The photodetector 83 is, for example, arranged at the output surface 305 with respect to the spectroscopic optical system 82 shown in FIG. 5 and configured by a multichannel photodetector in which a plurality of light detection elements that detect the intensity of wavelength components dispersed by the spectroscopic optical system 82 are aligned.

Next, a reflectivity measuring method according to the first embodiment will be described. Before the description, dark subtraction correction will be described. From the first detection unit 81 shown in FIG. 3, a weak signal is output even in the case where there is no entrance of the irradiation light L1 from the reference optical waveguide 50. Also, from the second detection unit 84, a weak signal is output even in the case where there is no entrance of the reflected light L2 from the second measurement optical waveguide 70. The weak signal is called a dark current. It is necessary to treat the dark current as a factor requiring calibration in the case where the intensity of light is acquired by a light detection element. Besides the dark current, a signal output from the first detection unit 81 and the second detection unit 84 include a signal caused by ambient light such as light from indoor lighting. The dark current described above and an unnecessary signal such as ambient light are collectively referred to as dark signal. In order to accurately acquire the spectrum waveform of the irradiation light L1 and the spectrum waveform of the reflected light L2, it is necessary to subtract the spectrum waveform of the dark signal from the spectrum waveform of the irradiation light L1 and the spectrum waveform of the reflected light L2.

A method of dark subtraction correction will be described with reference to FIG. 6. Herein, a method of performing dark subtraction correction for the irradiation light L1 will be described as an example. First, the measurement light source 30 is turned off, and the spectrum waveform of the dark signal is acquired by the spectroscopic detection unit 80. As shown in FIG. 6(*a*), the spectrum waveform of the dark signal includes a white noise component and a noise component having a peak in a particular wavelength region. The white noise component is a noise component due to dark current (FIG. 6(*b*)). The noise component having a peak of intensity in the particular wavelength region is a noise component due to ambient light or the like (FIG. 6(*c*)).

Next, the measurement light source 30 is turned on, and the spectrum waveform of the irradiation light L1 is acquired by the spectroscopic detection unit 80. As shown in FIG. 6(*d*), the spectrum waveform of the light includes a component of the spectrum waveform of the dark signal as shown in FIG. 6(*a*), for example, in addition to a component of the spectrum waveform of the irradiation light L1. Then, the spectrum waveform of the dark signal as shown in FIG. 6(*a*) is subtracted from the spectrum waveform including the component of the spectrum waveform of the irradiation light L1 and the component of the spectrum waveform of the dark signal as shown in FIG. 6(*d*). Accordingly, the spectrum waveform of the irradiation light L1 as shown in FIG. 6(*e*) not including the component of the spectrum waveform of the dark signal can be accurately acquired. For the reflected light L2 as well, the spectrum waveform of the reflected light L2 can be accurately acquired by subtracting the spectrum waveform of the dark signal obtained by turning off the measurement light source 30 from the spectrum waveform of the reflected light L2 obtained by turning on the measurement light source 30.

Figure 7:
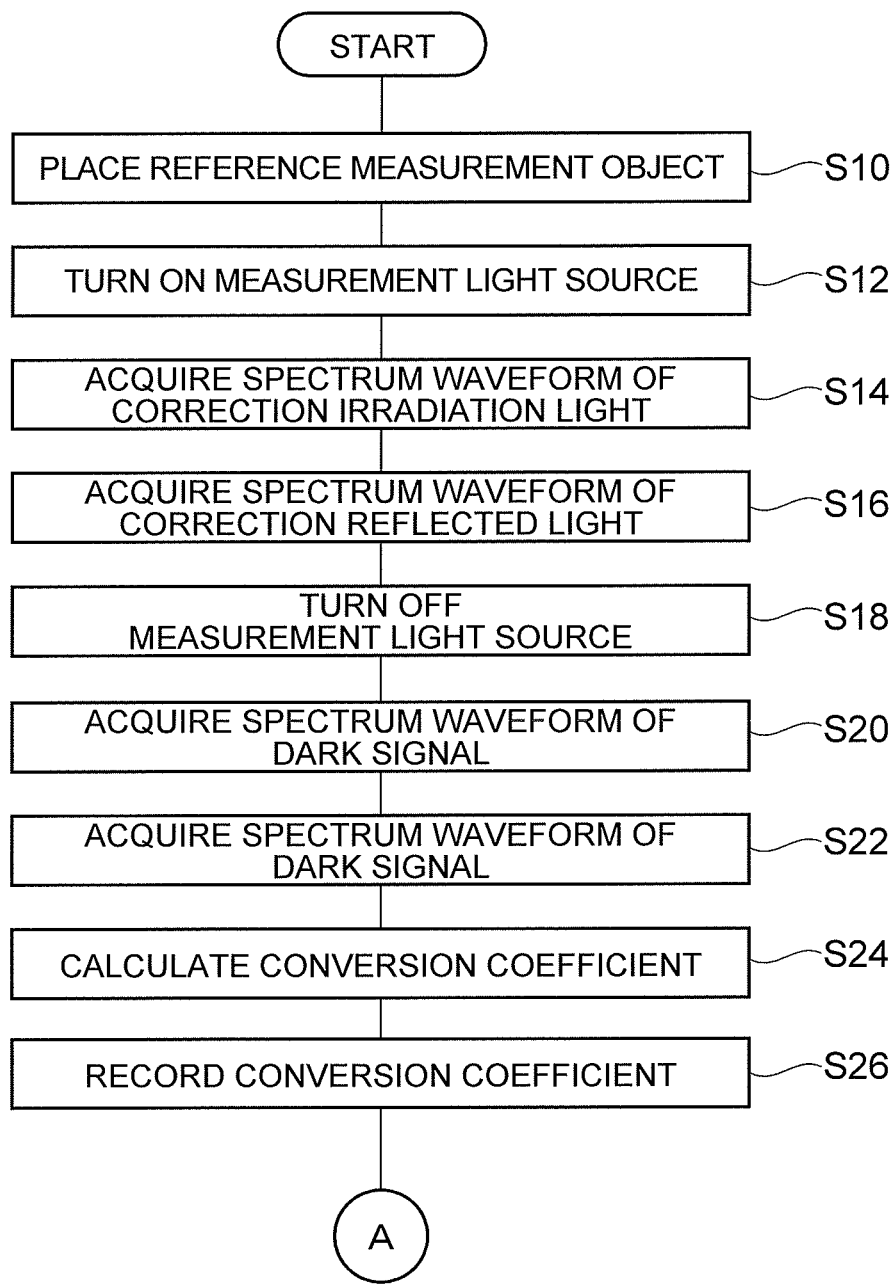
FIG. 7 is a flowchart showing the procedure of calculating a conversion coefficient according to the first embodiment.
Figure 8:
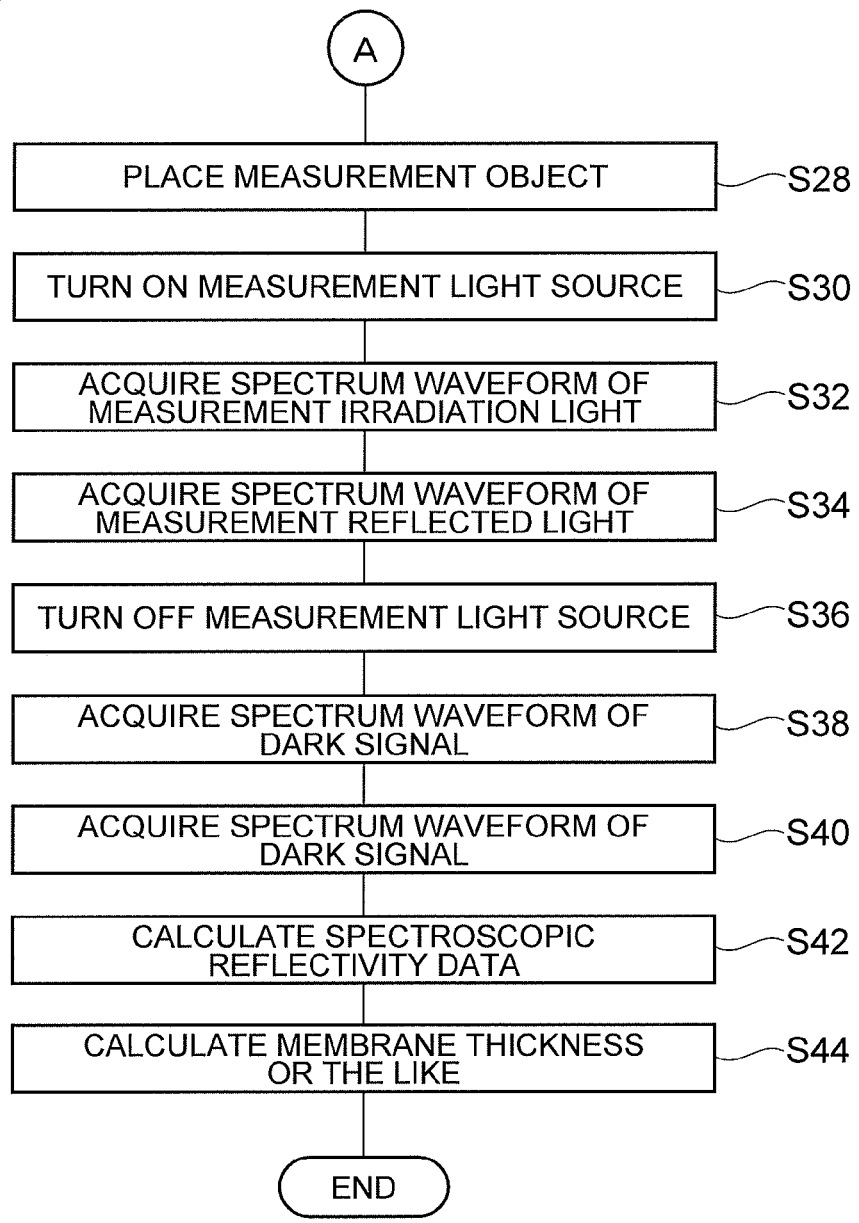
FIG. 8 is a flowchart showing the procedure of calculating the membrane thickness or the like according to the first embodiment.

Next, the reflectivity measuring method according to this embodiment using the dark subtraction correction will be described. FIG. 7 and FIG. 8 are flowcharts showing the reflectivity measuring method and a membrane thickness measuring method according to the first embodiment.

First, a step of calculating a conversion coefficient K (λ) shown in FIG. 7 is carried out. Herein, λ indicates a wavelength or a unit of wavelength dispersion for the spectroscopic detection unit. The reference measurement object of which spectroscopic reflectivity data Rref (λ) is known is placed in the sample measurement unit 11 (S 10). Next, the measurement light source 30 is turned on, and the reference light reception surface 51 and the irradiation light reception surface 61 are irradiated with the irradiation light L1 from the measurement light source 30. Herein, in the step of calculating the conversion coefficient K (λ), the irradiation light L1 from the measurement light source 30 is referred to as correction irradiation light. The correction irradiation light with which the irradiation light reception surface 61 is irradiated is supplied to the reference measurement object via the first measurement optical waveguide 60 and the measurement optical system 14 (correction irradiation light supply step S12).

The correction irradiation light with which the reference light reception surface 51 is irradiated is guided to the first detection unit 81 by the reference optical waveguide 50 and dispersed into wavelength components by the spectroscopic optical system 82. Then, a spectrum waveform Sref(λ) of the correction irradiation light is acquired by the photodetector 83 (correction irradiation light detection step S14).

Meanwhile, the correction irradiation light supplied to the reference measurement object is reflected on the surface of the reference measurement object and becomes the reflected light L2. Herein, the correction irradiation light reflected on the surface of the reference measurement object is referred to as correction reflected light. The correction reflected light is guided to the second detection unit 84 by the measurement optical system 14 and the second measurement optical waveguide 70 and is dispersed into wavelength components by the spectroscopic optical system 82. Then, a spectrum waveform Ssig (λ) of the correction reflected light is acquired by the photodetector 83 (first reflected light detection step S16). Next, the measurement light source 30 is turned off (S18). In this state, a spectrum waveform Dref (λ) of the dark signal output from the first detection unit 81 is acquired (S20). Further, a spectrum waveform Dsig (λ) of the dark signal output from the second detection unit 84 is acquired (S22).

Formula (1) shown below is a formula for calculating the conversion coefficient K (λ). Based on the spectroscopic reflectivity data Rref(λ) of the reference measurement object, the spectrum waveform Sref (λ) of the correction irradiation light, the spectrum waveform Ssig (λ) of the correction reflected light, the spectrum waveform Dref (λ) of the dark signal output from the first detection unit 81, and the spectrum waveform Dsig (λ) of the dark signal output from the second detection unit 84, the conversion coefficient K (λ) is calculated (coefficient calculation step S24). The calculation of the conversion coefficient K (λ) is executed in the coefficient calculation unit 91. The conversion coefficient K (λ) is recorded in the coefficient recording unit 92 (S26). Note that it suffices to carry out the step of calculating the conversion coefficient K (λ) described above at the time of a shipping inspection or in a routine maintenance work.

[Mathematical formula 1]

$$K(\lambda) = \frac{(Ssig(\lambda) - Dsig(\lambda))}{(Sref(\lambda) - Dref(\lambda)) \times Rref(\lambda)} \quad (1)$$

Next, a step of calculating spectroscopic reflectivity data Rsig (λ) of the measurement object shown in FIG. 8 is carried out. First, the measurement object is placed in the sample measurement unit 11 (placement step S28). Next, the measurement light source 30 is turned on, and the reference light reception surface 51 and the irradiation light reception surface 61 are irradiated with the irradiation light L1. Herein, in the calculation of the spectroscopic reflectivity data Rsig (λ) of the measurement object, the irradiation light L1 from the measurement light source 30 is referred to as measurement irradiation light. The measurement irradiation light with which the irradiation light reception surface 61 is irradiated is supplied to the measurement object via the first measurement optical waveguide 60 and the measurement optical system 14 (measurement irradiation light supply step S30).

The measurement irradiation light with which the reference light reception surface 51 is irradiated is guided to the first detection unit 81 by the reference optical waveguide 50 and dispersed into wavelength components by the spectroscopic optical system 82. Then, a spectrum waveform S'ref (λ) of the measurement irradiation light is acquired by the photodetector 83 (measurement irradiation light detection step S32). At this time, amount of time for which the spectrum waveform S'ref (λ) of the measurement irradiation light is acquired is set to arbitrary time length.

Meanwhile, the measurement irradiation light supplied to the measurement object is reflected on the surface of the measurement object and becomes the reflected light L2. Herein, the reflected light L2 is referred to as measurement reflected light. The measurement reflected light is guided to the second detection unit 84 by the measurement optical system 14 and the second measurement optical waveguide 70 and is dispersed into wavelength components by the spectroscopic optical system 82. Then, a spectrum waveform S'sig (λ) of the measurement reflected light is acquired by the photodetector 83 (second reflected light detection step S34). At this time, amount of time for which the spectrum waveform of the measurement reflected light is acquired is set to arbitrary time length.

Next, the measurement light source 30 is turned off (S36). At this time, amount of time for which the measurement light source 30 is turned off is set to about 100 milliseconds. Then, a spectrum waveform D'ref (λ) of the dark signal output from the first detection unit 81 is acquired (S38). At this time, amount of time for which the spectrum waveform D'ref (λ) of the dark signal is acquired is set to arbitrary time length. Also, in a state where the measurement light source 30 is turned off, a spectrum waveform D'sig (λ) of the dark signal output from the second detection unit 84 is acquired (S40). At this time, amount of time for which the spectrum waveform D'sig (λ) of the dark signal is acquired is set to arbitrary time length.

Formula (2) shown below is a formula for calculating the spectroscopic reflectivity data Rsig (λ). The numerator of formula (2) shows the spectrum waveform S'sig (λ) of the measurement reflected light not including the spectrum waveform D'sig (λ) of the dark signal. The denominator of formula (2) shows a value corresponding to the spectrum waveform of the measurement reflected light from the reference measurement object. By multiplying the conversion coefficient K (λ) and the waveform in which the spectrum waveform D'ref (λ) of the dark signal has been subtracted from the spectrum waveform S'ref (λ) of the measurement irradiation light, the value corresponding to the spectrum waveform of the measurement reflected light from the reference measurement object given by the denominator of formula (2) is calculated. Then, by dividing the waveform in which the spectrum waveform D'sig (λ) of the dark signal has been subtracted from the spectrum waveform S'sig (λ) of the measurement reflected light by the value corresponding to the spectrum waveform of the measurement reflected light from the reference measurement object, the spectroscopic reflectivity data Rsig (λ) of the measurement object is calculated (reflectivity calculation step S42). The calculation of the spectroscopic reflectivity data Rsig (λ) is executed in the reflectivity calculation unit 93.

[Mathematical formula 2]

$$Rsig(\lambda) = \frac{(S'sig(\lambda) - D'sig(\lambda))}{(S'ref(\lambda) - D'ref(\lambda)) \times K(\lambda)} \quad (2)$$

The spectroscopic reflectivity data Rsig (λ) measured by the reflectivity measuring device 1 in this embodiment is output to the membrane thickness calculation unit 19. In the membrane thickness calculation unit 19, the membrane thickness of the measurement object is calculated based on the spectroscopic reflectivity data Rsig (λ) (S44).

Regarding the membrane thickness measuring device 10 using the reflectivity measuring device 1 and the membrane thickness measuring method using the reflectivity measuring method according to this embodiment, a problem relating to fluctuation in the spectrum waveform of the measurement light source 30 will be first described and then an advantageous effect will be described.

Figure 9:
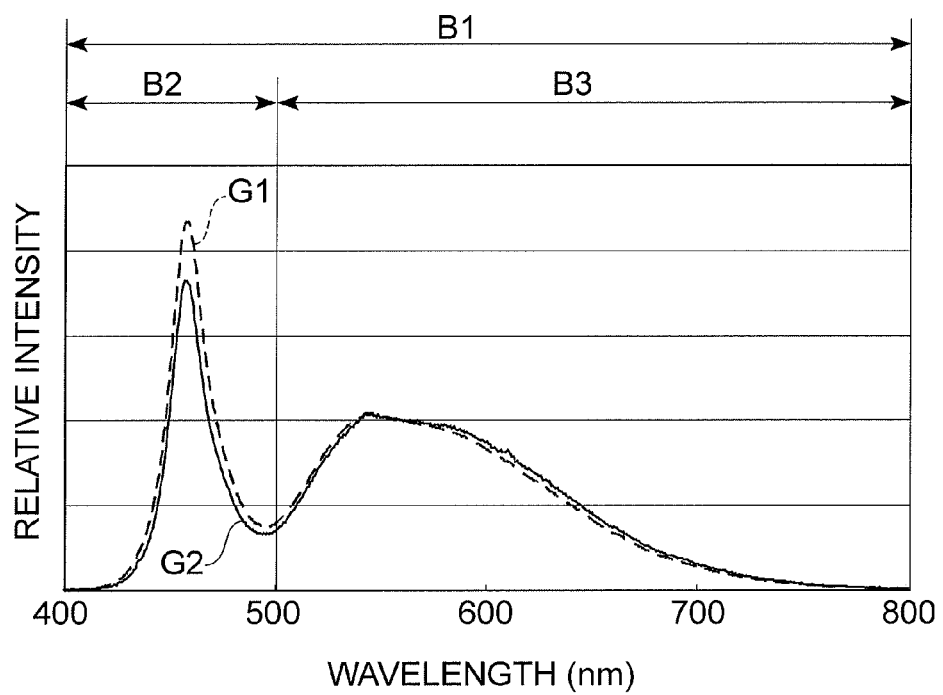
FIG. 9 is a graph showing the relationship of wavelength and each wavelength's relative intensity in the case where a phosphor-based white light-emitting diode is caused to emit light under different temperature environments.

The reflectivity measuring device 1 according to this embodiment includes the phosphor-based white LED 31 as a light source of the irradiation light L1 as shown in FIG. 4. Generally, with the white LED 31, it is known that the light amount of the excitation light fluctuates due to external cause such as heat given from a surrounding environment. FIG. 9 is a graph showing one example of the relationship of the wavelength and the wavelength-dependent relative intensity of white light generated from the white LED 31 under different temperature environments. In the wavelength region that the white light has, a region B1 in which the wavelength is 400 nm or more and 800 nm or less, for example, is the wavelength region to be measured. In the region B1, a region B2 in which the wavelength is 400 nm or more and 500 nm or less, for example, is the wavelength region of the excitation light, and a region B3 in which the wavelength is 500 nm or more and 800 nm or less, for example, is the wavelength region of fluorescence. A curve G1 in FIG. 9 shows the wavelength-dependent relative intensity of the white light in the case where the white LED 31 is caused to emit light under a temperature environment of room temperature, and a curve G2 shows the wavelength-dependent relative intensity of the white light in the case where the white LED 31 is caused to emit light under a temperature environment of 0° C. Comparing the curve G1 and the curve G2 in FIG. 9, peak values of the curve G1 and the curve G2 differ from each other in the region B2 that is the wavelength region of the excitation light. That is, in the case where the white LED 31 is caused to emit light under different temperature environments, the relative intensity in the wavelength region of the excitation light differs.

The difference of intensity of the excitation light in the wavelength region is not a problem in the case where the white LED 31 is used as a lighting equipment. However, it becomes a problem in the case where the white LED 31 is used in measurement where the wavelength region of excitation light is included in the wavelength region of measurement light. Note that the curve G1 and the curve G2 hardly differ in relative intensity in the region B3 that is the wavelength region of fluorescence. This is because the excitation light is supplied to the phosphor such that the phosphor is in a saturated state.

As shown in the example described above, the spectrum waveform of the irradiation light L1 from the white LED 31 included in the measurement light source 30 fluctuates due to external cause such as the surrounding temperature. For example, in the case where the temperature of the white LED 31 when acquiring the spectrum waveform of the reflected light L2 from the reference measurement object and the temperature of the white LED 31 when acquiring the spectrum waveform of the reflected light L2 from the measurement object differ from each other, the correction irradiation light with which the reference measurement object is irradiated and the measurement irradiation light with which the measurement object is irradiated differs from each other in the wavelength-dependent relative intensity in the wavelength region of the excitation light. Therefore, the spectroscopic reflectivity data Rsig (λ) of the measurement object cannot be accurately measured.

With the reflectivity measuring device 1 and the reflectivity measuring method according to this embodiment, the value corresponding to the spectrum waveform of the measurement reflected light from the reference measurement object can be calculated for each measurement from the conversion coefficient K (λ) and the spectrum waveform S'ref (λ) of the measurement irradiation light with which the measurement object is irradiated without using the reference measurement object upon measurement of the measurement object. Accordingly, when calculating the spectroscopic reflectivity data Rsig (λ) of the measurement object, the value corresponding to the spectrum waveform of the measurement reflected light including the influence of fluctuation in the irradiation light L1 can be used. That is, even in the case where the spectrum waveform S'ref (λ) of the measurement irradiation light fluctuates, it is possible to cancel the fluctuation in the spectrum waveform S'ref (λ) of the measurement irradiation light included in the spectrum waveform S'sig (λ) of the measurement reflected light. Thus, the spectroscopic reflectivity data Rsig (λ) of the measurement object can be accurately measured constantly. Note that the conversion coefficient K (λ) is not subject to influence even if the spectrum waveform S'ref (λ) fluctuates.

Further, with the membrane thickness measuring device 10 including the reflectivity measuring device according to this embodiment and the membrane thickness measuring method including the reflectivity measuring method according to this embodiment, it is possible to accurately calculate the spectroscopic reflectivity data Rsig (λ) of the measurement object, and therefore the membrane thickness of the measurement object obtained from the spectroscopic reflectivity data Rsig (λ) can be accurately calculated.

Due to the accurate spectroscopic reflectivity data Rsig (λ) being obtained, variation in the spectroscopic reflectivity data Rsig (λ) in the case where reflectivity measurement is done a plurality of times for the same measurement object can be reduced. Thus, variation in a measured value of the membrane thickness of the measurement object calculated from the spectroscopic reflectivity data Rsig (λ) can be reduced.

In the case where there is fluctuation in the spectrum waveform of the irradiation light L1 at a production site, the spectrum waveform of the measurement reflected light from the reference measurement object has been acquired using the reference measurement object for each measurement to re-set the acquired spectrum waveform. With this method, it is necessary to acquire the spectrum waveform of the measurement reflected light from the reference measurement object and temporarily stop a production line for re-setting. Therefore, it has been a cause of reducing the production efficiency in a production line.

With the reflectivity measuring device 1 and the reflectivity measuring method according to this embodiment, the value corresponding to the spectrum waveform of the measurement reflected light from the reference measurement object is calculated from the spectrum waveform S'ref (λ) of the measurement irradiation light and the conversion coefficient K (λ). Thus, it is possible to calculate the spectroscopic reflectivity data Rsig (λ) without acquiring the spectrum waveform of the measurement reflected light from the reference measurement object for each measurement. Accordingly, even in the case where there is fluctuation in the spectrum waveform of the irradiation light L1, the spectroscopic reflectivity data Rsig (λ) can be accurately measured without carrying out a step of acquiring the value corresponding to the spectrum waveform of the measurement reflected light from the reference measurement object for each measurement. Further, since process steps can be reduced, a reduction in the production efficiency can be prevented, and a reduction in cost is possible.

Figure 10:
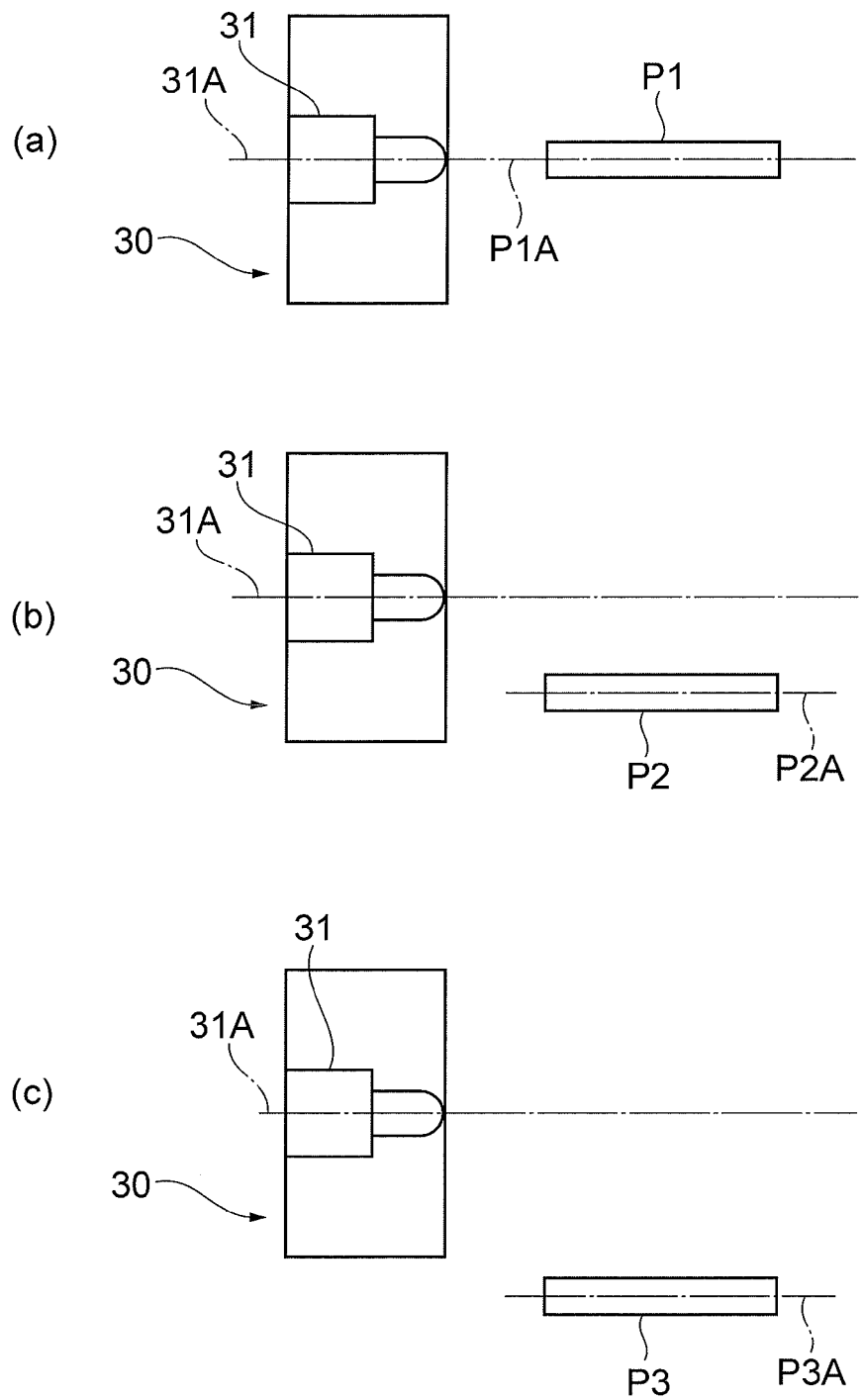
FIG. 10(a) is a view showing one example of the arrangement of a phosphor-based white light-emitting diode and an optical waveguide.
FIG. 10(b) is a view showing another example of the arrangement of the phosphor-based white light-emitting diode and the optical waveguide.
FIG. 10(c) is a view showing still another example of the arrangement of the phosphor-based white light-emitting diode and the optical waveguide.

Next, with reference to FIG. 10 and FIG. 11, a problem of the spectrum waveform differing due to the positional relationship of the reference optical waveguide 50 as well as the first measurement optical waveguide 60 and the measurement light source 30 including the white LED 31 will be described, and then a solution to the problem as an advantageous effect of this embodiment will be described. FIG. 10(a) shows a form in which an optical waveguide P1 is arranged in a position such that the white LED 31 and the optical waveguide P1 are opposed with the axis 31A passing through the white LED 31 and a central axis NA of the optical waveguide P1 coincide. FIG. 10(b) shows a form in which an optical waveguide P2 is arranged in a position such that the axis 31A passing through the white LED 31 and a central axis P2A of the optical waveguide P2 are apart. FIG. 10(c) shows a form in which the optical waveguide P2 is arranged in a position such that the axis 31A passing through the white LED 31 and a central axis P3A of the optical waveguide P3 are further apart.

Figure 11:
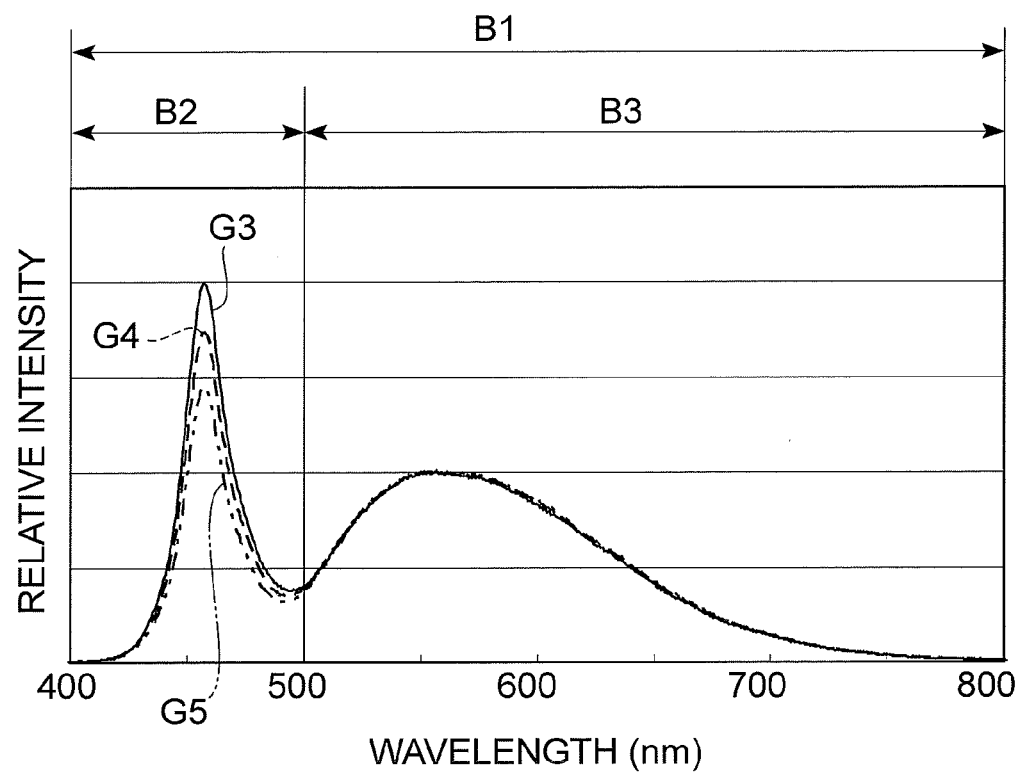
FIG. 11 is a graph showing the relationship of wavelength and each wavelength's relative intensity of irradiation light that has entered the waveguide shown in FIG. 10.

FIG. 11 is a graph showing the wavelength-dependent relative intensity of the irradiation light L1 that has entered the optical waveguides P1 to P3 shown in FIG. 10. In a similar manner as in FIG. 9, B1 is the wavelength region to be measured, B2 is the wavelength region of the excitation light, and B3 is the wavelength region of fluorescence. A curve G3 is the wavelength-dependent relative intensity of the irradiation light L1 that has entered the optical waveguide P1, a curve G4 is the wavelength-dependent relative intensity of the irradiation light L1 that has entered the optical waveguide P2, and a curve G5 is the wavelength-dependent relative intensity of the irradiation light L1 that has entered the optical waveguide P3.

As shown in FIG. 11, the wavelength-dependent relative intensity of the irradiation light L1 that has entered the respective optical waveguides P1 to P3 are approximately the same in the wavelength region (B3) of fluorescence. However, peak values differ from each other in the wavelength region (B2) of the excitation light. That is, the spectrum waveforms differ from each other in the wavelength region of the excitation light depending on the positional relationship of the reference optical waveguide 50 as well as the first measurement optical waveguide 60 and the white LED 31.

Figure 12:
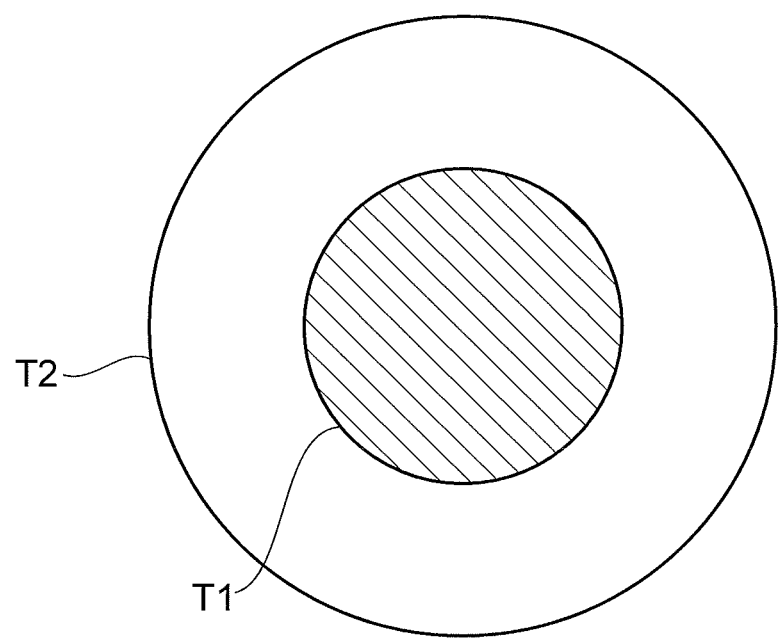
FIG. 12 is a conceptual diagram schematically showing the section of an irradiation range of irradiation light.

In the case of the phosphor-based white LED 31, light from a light-emitting element becomes the excitation light with which phosphor is irradiated to generate fluorescence. FIG. 12 is a conceptual diagram showing the section of an irradiation range of the irradiation light L1. Since there is directionality in the excitation light, a center portion T1 in the section of the irradiation range of the irradiation light L1 is a region where the influence of the excitation light is strong. Also, since there is a wide-range characteristic in fluorescence, a surrounding portion T2 in the section of the irradiation range of the irradiation light L1 is a region where the influence of fluorescence is strong. Therefore, it is considered that the spectrum waveforms of the irradiation light L1 that has entered the optical waveguides P1 to P3 differ from each other depending on the positional relationship of the measurement light source 30 the optical waveguides P1 to P3.

In the membrane thickness measuring device 10 using the reflectivity measuring device 1 according to this embodiment, the reference optical waveguide 50 and the first measurement optical waveguide 60 are arranged, as shown in FIG. 4, such that the central axis 50A of the reference optical waveguide 50 and the central axis 60A of the first measurement optical waveguide 60 are line symmetrical with respect to the axis 31A passing through the white LED 31.

Figure 13:
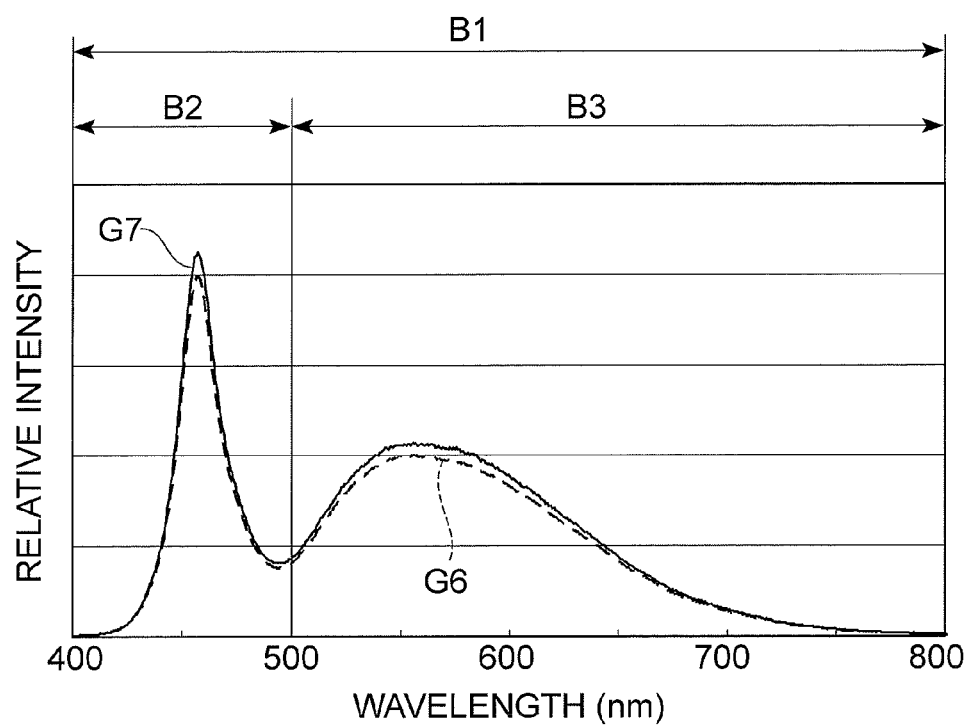
FIG. 13 is a graph showing the relationship of wavelength and each wavelength's relative intensity of irradiation light that has entered the reference optical waveguide and the first measurement optical waveguide.

FIG. 13 shows the wavelength-dependent relative intensity of the irradiation light L1 with which the reference optical waveguide 50 and the first measurement optical waveguide 60 are irradiated in the case of such an arrangement. In a similar manner as in FIG. 9, B1 is the wavelength region to be measured, B2 is the wavelength region of the excitation light, and B3 is the wavelength region of fluorescence. A curve G6 shows the wavelength-dependent relative intensity of the irradiation light L1 with which the reference optical waveguide 50 is irradiated, and a curve G7 shows the wavelength-dependent relative intensity of the irradiation light L1 with which the first measurement optical waveguide 60 is irradiated. In the case where the central axis 50A of the reference optical waveguide 50 and the central axis 60A of the first measurement optical waveguide 60 are arranged to be line symmetrical with respect to the axis 31A passing through the white LED 31, the difference in the spectrum waveform of the irradiation light L1 with which the reference optical waveguide 50 and the first measurement optical waveguide 60 are irradiated is reduced. Thus, with the membrane thickness measuring device 10 using the reflectivity measuring device 1 according to this embodiment, the difference of the spectrum waveform of the irradiation light L1 with which the reference optical waveguide 50 is irradiated and the spectrum waveform of the irradiation light L1 with which the first measurement optical waveguide 60 is irradiated can be reduced, and the spectroscopic reflectivity data Rsig ($\lambda$) can be accurately measured.

The reflectivity measuring device 1 according to this embodiment includes the white LED 31 as the measurement light source 30. The life span of the white LED 31 is longer than for a lamp light source such as a conventionally-used xenon lamp or halogen lamp of which the life span is about 1000 hours. Accordingly, the number of times for replacement of the light source that the measurement light source 30 includes can be reduced.

The reflectivity measuring device 1 according to this embodiment includes the reference optical waveguide 50 and the first measurement optical waveguide 60. With such a configuration, it is possible to adjust the arrangement of the respective optical waveguides. Accordingly, the each wavelength's intensity of the irradiation light L1 with which the reference optical waveguide 50 and the first measurement optical waveguide 60 are irradiated can be adjusted.

In the reflectivity measuring device 1 according to this embodiment, the spectroscopic detection unit 80 includes the first detection unit 81 and the second detection unit 84. With such a configuration, the detection unit that acquires the spectrum waveform of the irradiation light L1 and the detection unit that acquires the spectrum waveform of the reflected light L2 from the measurement object can be made independent from each other. Thus, it is possible to simultaneously acquire the spectrum waveform of the irradiation light L1 and the spectrum waveform of the reflected light L2 from the measurement object, and further the spectroscopic reflectivity data Rsig ($\lambda$) of the measurement object can be accurately measured. Further, time required for measurement of the each wavelength's reflectivity can be shortened.

The reflectivity measuring device 1 according to this embodiment calculates the spectroscopic reflectivity data Rsig ($\lambda$) with formula (2) described above. By using formula (2), the spectroscopic reflectivity data Rsig ($\lambda$) can be easily calculated. Further, with formula (2), the spectroscopic reflectivity data Rsig ($\lambda$) can be calculated without using the spectroscopic reflectivity data Rref ($\lambda$) of the reference measurement object. Thus, the reflectivity measuring device 1 can be configured without including a device that records the spectroscopic reflectivity data Rref ($\lambda$) of the measurement object.

Second Embodiment

Figure 14:
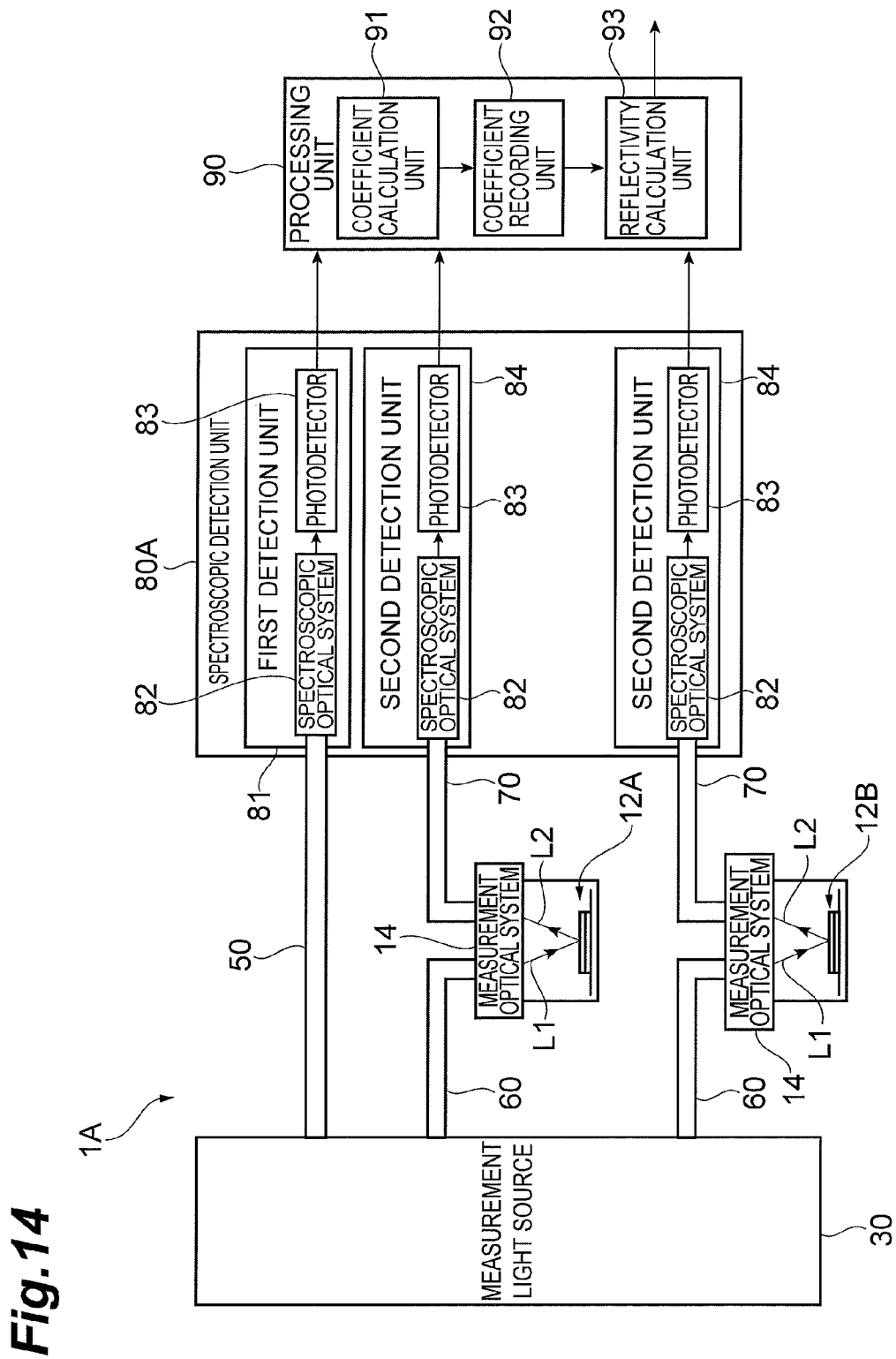
FIG. 14 is a block diagram showing the configuration of a second embodiment for the reflectivity measuring device.

Subsequently, a second embodiment will be described. FIG. 14 shows one example of the configuration of a reflectivity measuring device 1A according to the second embodiment. The difference of this embodiment shown in FIG. 14 and the first embodiment described above is that it is configured to enable simultaneous measurement of a plurality of samples 12. That is, the reflectivity measuring device 1A according to this embodiment is configured to include a plurality of first measurement optical waveguides 60, measurement optical systems 14, second measurement optical waveguides 70, and second detection units 84. Herein, in this embodiment, a case where spectroscopic reflectivity data Rsig (n, $\lambda$) for each of two samples 12 is calculated will be described as an example in this embodiment. Note that, with the reflectivity measuring device 1A according to this embodiment, there may be two or more of the samples 12.

Next, the configuration of the reflectivity measuring device 1A according to this embodiment will be described. Note that, herein, only the configuration differing from the first embodiment will be described. The reflectivity measuring device 1A is configured to include the measurement light source 30, the reference optical waveguide 50, two first measurement optical waveguides 60, two second measurement optical waveguides 70, a spectroscopic detection unit 80A, and the processing unit 90.

The spectroscopic detection unit 80A according to this embodiment is configured to include the first detection unit 81 that acquires the spectrum waveform of the irradiation light L1 and two second detection units 84 that acquire the spectrum waveform of the reflected light L2 from samples 12A and 12B. To the spectroscopic optical system 82 of one second detection unit 84, the other end of the second measurement optical waveguide 70 that guides the reflected light L2 from one of the samples 12A and 12B is optically coupled. To the spectroscopic optical system 82 of the other second detection unit 84, the other end of the second measurement optical waveguide 70 that guides the reflected light L2 from the other one of the samples 12A and 12B is optically coupled.

The irradiation light L1 from the measurement light source 30 is supplied to the samples 12A and 12B via the first measurement optical waveguides 60 and the measurement optical systems 14. The irradiation lights L1 supplied to the samples 12A and 12B are reflected on the surface of the samples 12A and 12B and becomes the reflected lights L2. The reflected lights L2 are supplied to the spectroscopic optical systems 82 of the second detection units 84 via the measurement optical systems 14 and the second measurement optical waveguides 70. The reflected lights L2 supplied to the spectroscopic optical systems 82 are dispersed to be detectable at multi-wavelength. Then, the spectrum waveforms of the reflected lights L2 are acquired by the photodetectors 83.

Next, a reflectivity measuring method according to this embodiment using dark subtraction correction will be described. Note that the principle of the dark subtraction correction is the same as the principle described in the first embodiment. The difference of this embodiment and the first embodiment is that it is different in that one conversion coefficient K (λ) is calculated in the first embodiment while a conversion coefficient K (n, λ) is calculated for each second detection unit 84 is calculated in this embodiment. Herein, n is an integer where n=1 to 2 in this embodiment. This embodiment differs from the first embodiment in that the spectroscopic reflectivity data Rsig (n, λ) is calculated for each of the plurality of samples 12. In the procedure of the reflectivity measuring method according to this embodiment, the procedure other than the differences described above is similar to the first embodiment.

First, in this embodiment, the conversion coefficient K (n, λ) is calculated for each of the two second detection units 84. Formula (3) shown below is a formula for calculating the conversion coefficient K (n, λ). Based on a spectrum waveform S sin (n, λ) of correction reflected light from a reference measurement object, the spectrum waveform Sref (λ) of correction irradiation light, a spectrum waveforms Dsig (n, λ) and Dref (λ) of dark signals, and the known spectroscopic reflectivity data Rref (λ) of the reference measurement object, the conversion coefficient K (n, λ) is calculated.

[Mathematical formula 3]

$$K(n, \lambda) = \frac{(Ssig(n, \lambda) - Dsig(n, \lambda))}{(Sref(\lambda) - Dref(\lambda)) \times Rref(\lambda)} \quad (3)$$

Next, the spectroscopic reflectivity data Rsig (n, λ) of the samples 12A and 12B is calculated. Formula (4) shown below is a formula for calculating the spectroscopic reflectivity data Rsig (n, λ). Based on a spectrum waveform S' sin(n, λ) of measurement reflected light from a measurement object, the spectrum waveform S'ref (λ) of measurement irradiation light, spectrum waveforms D'sig (n, λ) and D'ref (λ) of dark signals, and the conversion coefficient K (n, λ), the spectroscopic reflectivity data Rsig (n, λ) of the samples 12A and 12B is calculated.

[Mathematical formula 4]

$$Rsig(n, \lambda) = \frac{(S'sig(n, \lambda) - D'sig(n, \lambda))}{(S'ref(\lambda) - D'ref(\lambda)) \times K(n, \lambda)} \quad (4)$$

With the reflectivity measuring device 1A and the reflectivity measuring method using the reflectivity measuring device 1A of this embodiment, the spectroscopic reflectivity data Rsig (n, λ) of a plurality of measurement objects can be measured. In addition, the spectroscopic reflectivity data Rsig (n, λ) of a plurality of measurement objects can be measured simultaneously. Further, with the membrane thickness measuring device 10 including the reflectivity measuring device 1A and the membrane thickness measuring method using the membrane thickness measuring device 10 of this embodiment, the membrane thickness of a plurality of measurement objects can be measured simultaneously.

Third Embodiment

Figure 15:
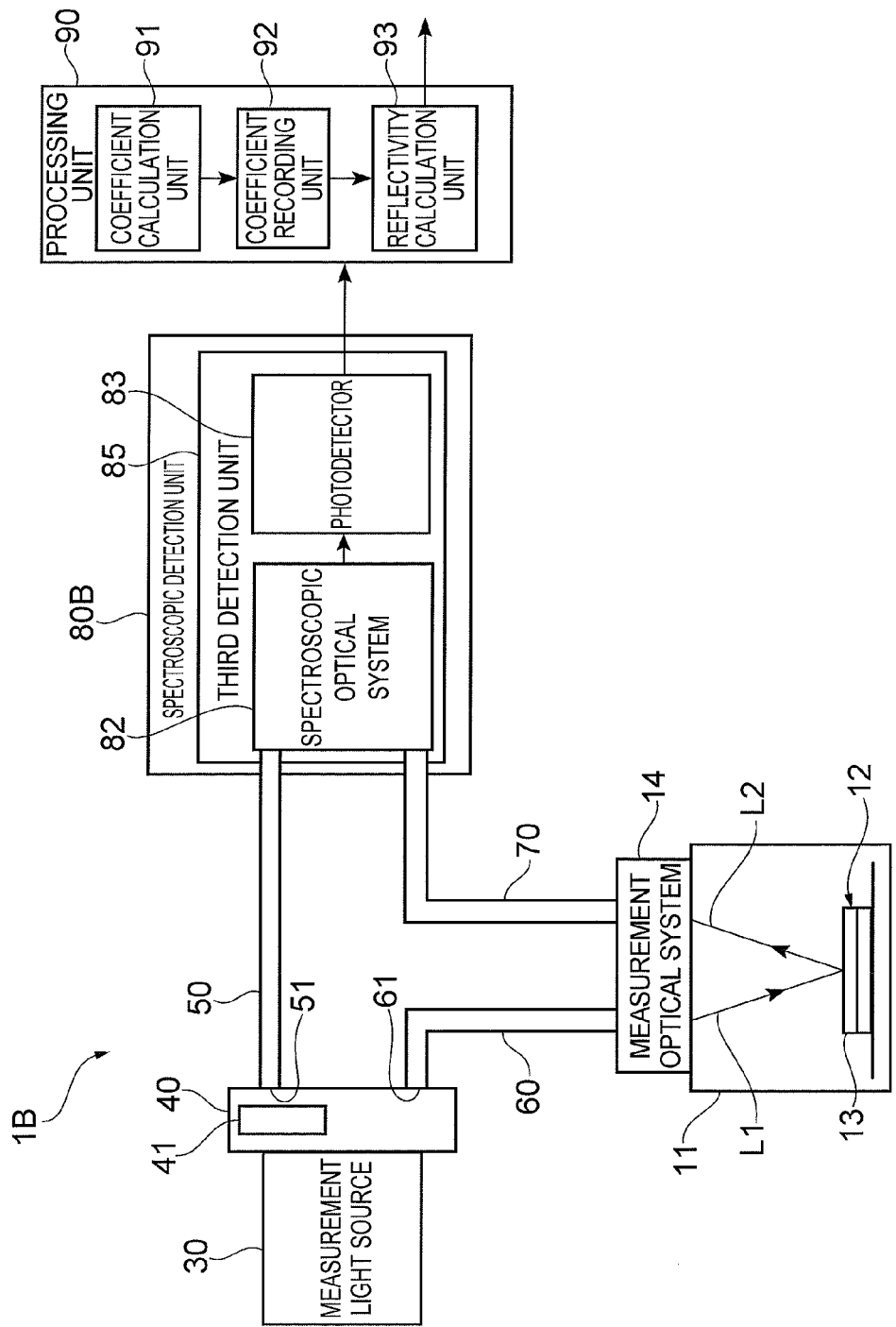
FIG. 15 is a block diagram showing the configuration of a third embodiment for the reflectivity measuring device.

Subsequently, a third embodiment will be described. FIG. 15 shows one example of the configuration of a reflectivity measuring device 1B according to the third embodiment. The difference of the first embodiment described above and this embodiment is that, as shown in FIG. 15, a spectroscopic detection unit 80B is configured by a third detection unit 85. That is, in this embodiment, the configuration in which the spectrum waveform of the irradiation light L1 and the spectrum waveform of the reflected light L2 are acquired by the third detection unit 85 differs from the first embodiment. Further, the difference of the first embodiment described above and this embodiment is that the reflectivity measuring device 1B according to this embodiment includes optical waveguide selecting device 40. Note that the device configuration other than the spectroscopic detection unit 80B and the optical waveguide selecting device 40 is similar to the first embodiment.

First, the configuration of the reflectivity measuring device 1B used in this embodiment as shown in FIG. 15 will be described. Note that, herein, only the configuration differing from the first embodiment will be described. To the measurement light source 30, the optical waveguide selecting device 40 is optically coupled. The optical waveguide selecting device 40 is configured to include a shutter 41. With the shutter 41, at least one of the reference optical waveguide 50 and the first measurement optical waveguide 60 can be selectively irradiated with the irradiation light L1. Also, both the reference optical waveguide 50 and the first measurement optical waveguide 60 can be kept from being irradiated.

In the reference optical waveguide 50, one end to which the reference light reception surface 51 is provided is optically coupled with the optical waveguide selecting device 40, and the other end is optically coupled to the spectroscopic optical system 82 in the third detection unit 85. In the first measurement optical waveguide 60, one end to which the irradiation light reception surface 61 is provided is optically coupled with the optical waveguide selecting device 40. Also, in the second measurement optical waveguide 70, the other end is optically coupled to the spectroscopic optical system 82 in the third detection unit 85.

Figure 16:
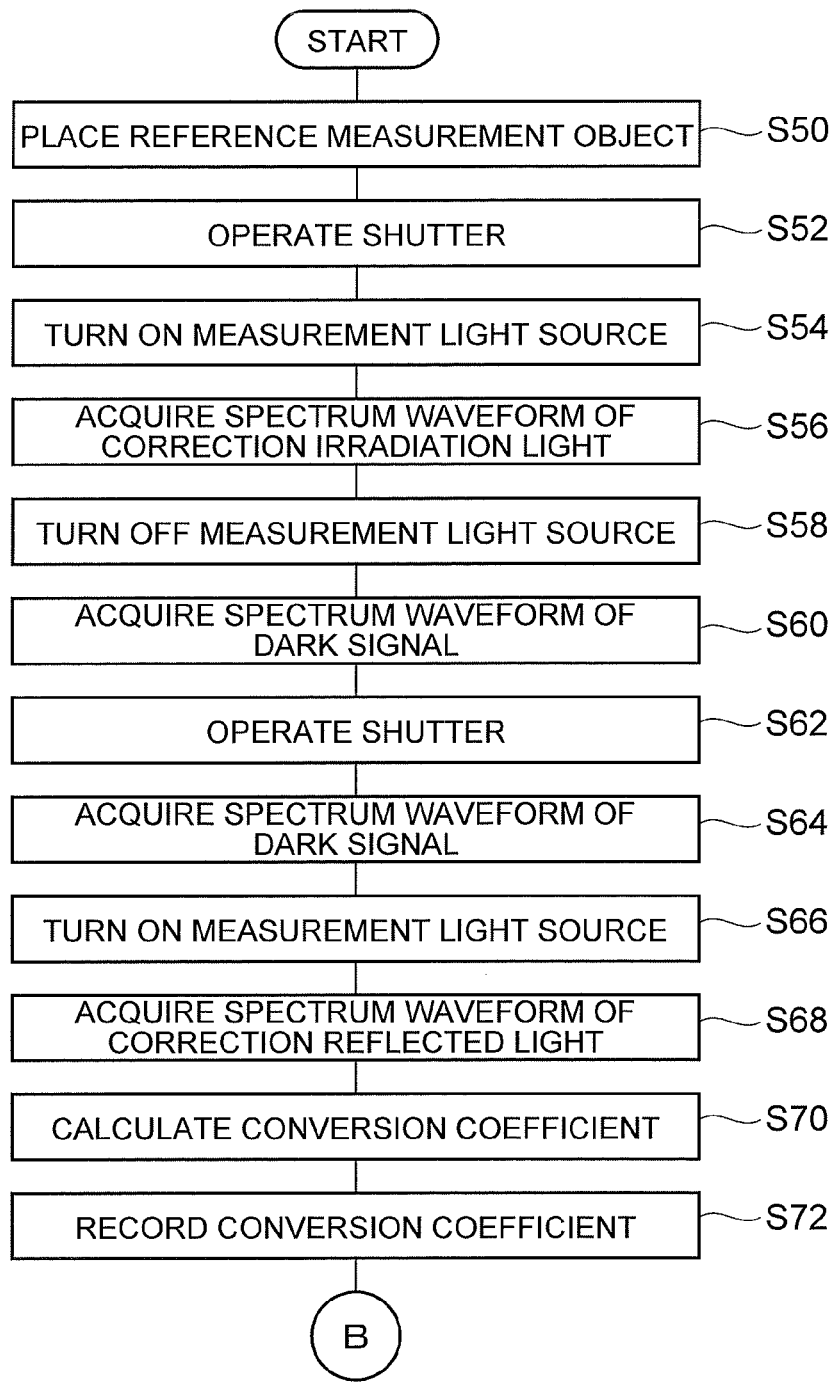
FIG. 16 is a flowchart showing the procedure of calculating a conversion coefficient according to the third embodiment.
Figure 17:
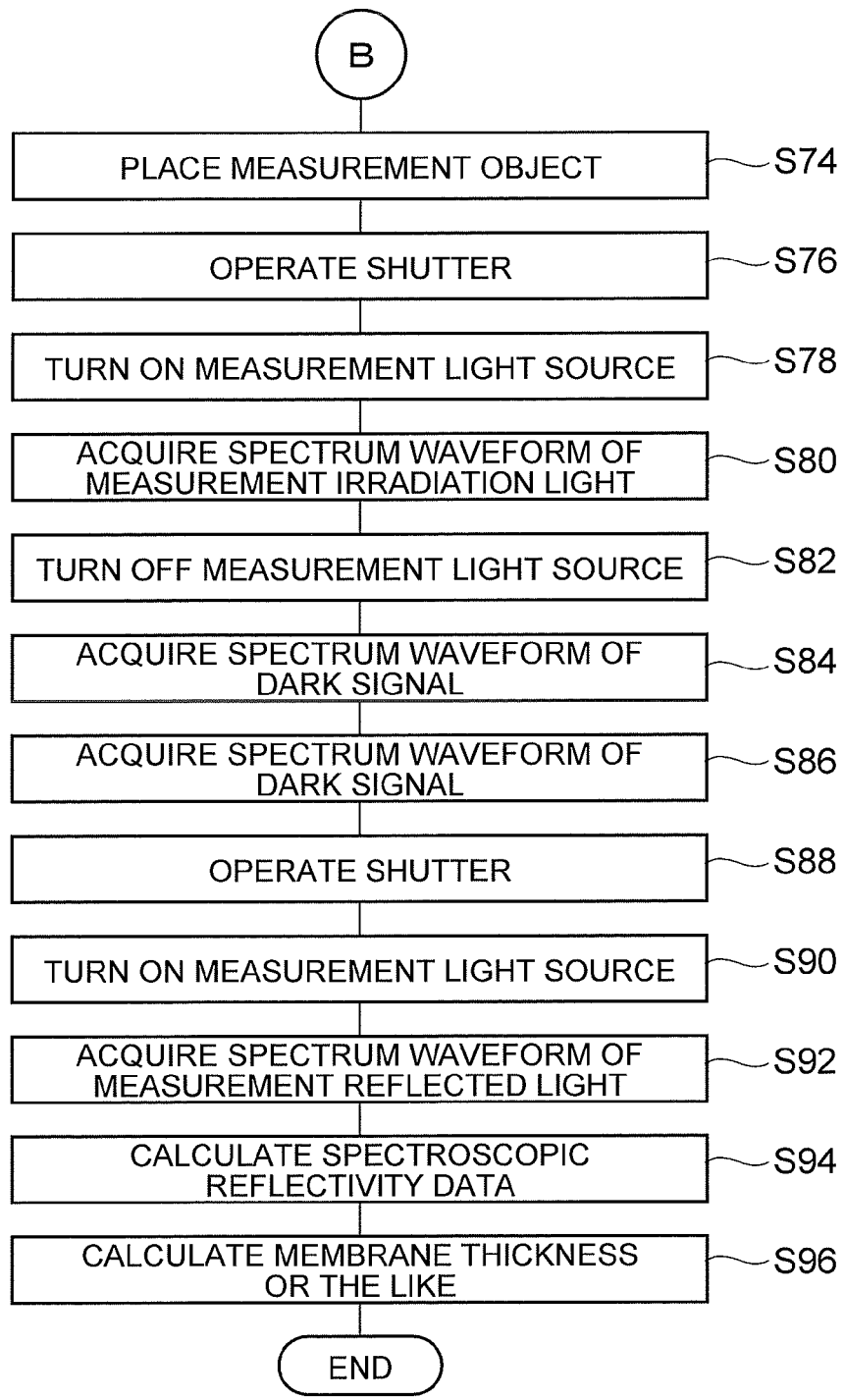
FIG. 17 is a flowchart showing the procedure of calculating the membrane thickness or the like according to the third embodiment.

Next, a reflectivity measuring method according to the third embodiment using dark subtraction correction will be described. FIG. 16 and FIG. 17 are flowcharts showing a membrane thickness measuring method using the reflectivity measuring method according to this embodiment. Note that the principle of the dark subtraction correction is the same as the principle described in the first embodiment.

First, a step of calculating the conversion coefficient K (λ) shown in FIG. 16 is carried out. As a method of calculating the conversion coefficient K (λ) in this embodiment, a method of calculating the conversion coefficient K (λ) by controlling the measurement light source 30 to acquire the spectrum waveform of the dark signal will be described.

A reference measurement object of which the spectroscopic reflectivity data Rref (λ) is known is placed in the sample measurement unit 11 (S50). Next, the optical waveguide selecting device 40 is controlled to operate the shutter 41 such that irradiation of the irradiation light L1 to the irradiation light reception surface 61 is blocked and the irradiation light L1 is incident only upon the reference light reception surface 51 (S52). The amount of time it takes to operate the shutter 41 is about 100 milliseconds. Next, the measurement light source 30 is turned on, and the reference light reception surface 51 is irradiated with the irradiation light L1 from the measurement light source 30 (S54). Herein, in the step of calculating the conversion coefficient K (λ), the irradiation light L1 from the measurement light source 30 is referred to as correction irradiation light.

The correction irradiation light with which the reference light reception surface 51 is irradiated is guided to the third detection unit 85 by the reference optical waveguide 50. The correction irradiation light guided to the third detection unit 85 is dispersed into wavelength components by the spectroscopic optical system 82. Then, the spectrum waveform Sref (λ) of the correction irradiation light is acquired by the photodetector 83 (correction irradiation light detection step S56). Note that amount of time for which the spectrum waveform Sref (λ) of the correction irradiation light is acquired is set to arbitrary time length. Next, the measurement light source 30 is turned off (S58). Amount of time for which the measurement light source 30 is turned off is set to about the same length as the amount of time for which the spectrum waveform Sref (λ) of the correction irradiation light is acquired. Then, the spectrum waveform Dref (λ) of the dark signal output from the third detection unit 85 is acquired (S60).

Next, the optical waveguide selecting device 40 is controlled to operate the shutter 41 such that irradiation of the correction irradiation light to the reference light reception surface 51 is blocked and only the irradiation light reception surface 61 is irradiated with the correction irradiation light (S62). The amount of time it takes to operate the shutter 41 is about 100 milliseconds. In this state, the spectrum waveform Dsig (λ) of the dark signal output from the third detection unit 85 is acquired (S64). At this time, amount of time for which the spectrum waveform Dsig (λ) of the dark signal is acquired is set to about the same length as the amount of time for which the spectrum waveform Ssig (λ) of the correction reflected light is acquired. Note that, herein, Dref (λ) described above may be used as Dsig (λ).

Next, the measurement light source 30 is turned on. The correction irradiation light with which the irradiation light reception surface 61 is irradiated is supplied to the reference measurement object via the first measurement optical waveguide 60 and the measurement optical system 14 (correction irradiation light supply step S66). The correction irradiation light supplied to the reference measurement object is reflected on the surface of the reference measurement object and becomes the reflected light L2. Herein, the reflected light L2 is referred to as correction reflected light. The correction reflected light is guided to the third detection unit 85 by the measurement optical system 14 and the second measurement optical waveguide 70 and is dispersed into wavelength components by the spectroscopic optical system 82. Then, the spectrum waveform Ssig (λ) of the correction reflected light is acquired by the photodetector 83 (first reflected light detection step S68). At this time, amount of time for which the spectrum waveform Ssig (λ) of the correction reflected light is acquired is set to predetermined time length.

Formula (5) shown below is a formula for calculating the conversion coefficient K (λ). Based on the spectroscopic reflectivity data Rref (λ) of the reference measurement object, the spectrum waveform Sref (λ) of the correction irradiation light, the spectrum waveform Ssig (λ) of the correction reflected light, and the spectrum waveforms Dref (λ) and Dsig (λ) of the dark signals output from the third detection unit 85, the conversion coefficient K (λ) is calculated (coefficient calculation step S70). The calculation of the conversion coefficient K (λ) is executed in the coefficient calculation unit 91. The conversion coefficient K (λ) is recorded in the coefficient recording unit 92 (S72). Note that it suffices to carry out the step of calculating the conversion coefficient K (λ) described above at the time of a shipping inspection or in a routine maintenance work.

[Mathematical formula 5]

$$K(\lambda) = \frac{(Ssig(\lambda) - Dsig(\lambda))}{(Sref(\lambda) - Dref(\lambda)) \times Rref(\lambda)} \quad (5)$$

Next, a step of calculating spectroscopic reflectivity data Rsig (λ) of a measurement object shown in FIG. 17 is carried out. First, the measurement object is placed in the sample measurement unit 11 (placement step S74). Next, the optical waveguide selecting device 40 is controlled to operate the shutter 41 such that the irradiation light L1 from the measurement light source 30 is incident upon the reference light reception surface 51 (S76). Next, the measurement light source 30 is turned on, and the reference light reception surface 51 is irradiated with the irradiation light L1 (S78). Herein, in the case where the spectroscopic reflectivity data Rsig (λ) of the measurement object is calculated, the irradiation light L1 from the measurement light source 30 is referred to as measurement irradiation light.

The measurement irradiation light with which the reference light reception surface 51 is irradiated is supplied to the third detection unit 85 via the reference optical waveguide 50. The measurement irradiation light supplied to the third detection unit 85 is dispersed into wavelength components by the spectroscopic optical system 82. Then, the spectrum waveform S'ref (λ) of the measurement irradiation light is acquired by the photodetector 83 (measurement irradiation light detection step S80).

Next, the measurement light source 30 is turned off (S82). In this state, the spectrum waveform D'ref (λ) of the dark signal output from the third detection unit 85 is acquired (S84). Next, the spectrum waveform D'sig (λ) of the dark signal output from the third detection unit 85 is acquired (S86). Note that it may be such that only D'ref (λ) out of D'ref (λ) and D'sig (λ) described above is acquired, and D'ref (λ) that has been acquired is used as D'sig (λ). Conversely, it may be such that only D'sig (λ) out of D'ref (λ) and D'sig (λ) described above is acquired, and D'sig (λ) that has been acquired is used as D'ref (λ).

Next, the optical waveguide selecting device 40 is controlled to operate the shutter 41 such that irradiation of the measurement irradiation light to the reference light reception surface 51 is blocked and only the irradiation light reception surface 61 is irradiated with the measurement irradiation light (S88). Next, the measurement light source 30 is turned on. The measurement irradiation light with which the irradiation light reception surface 61 is irradiated is supplied to the measurement object via the first measurement optical waveguide 60 and the measurement optical system 14 (measurement irradiation light supply step S90).

The measurement irradiation light supplied to the measurement object is reflected on the surface of the measurement object and becomes the reflected light L2. Herein, the reflected light L2 is referred to as measurement reflected light. The measurement reflected light is guided to the third detection unit 85 by the measurement optical system 14 and the second measurement optical waveguide 70 and is dispersed into wavelength components by the spectroscopic optical system 82. Then, the spectrum waveform S'sig (λ) of the measurement reflected light is acquired by the photodetector 83 (second reflected light detection step S92).

Formula (6) shown below is a formula for calculating the spectroscopic reflectivity data Rsig (λ). Based on the spectrum waveform S'ref (λ) of the measurement irradiation light, the spectrum waveform D'ref (λ) of the dark signal, and the conversion coefficient K (λ), a value corresponding to the spectrum waveform of the measurement reflected light from the reference measurement object given by the denominator of formula (6) is calculated. Then, based on the spectrum waveform S'sig (λ) of the measurement reflected light, the spectrum waveform D'sig (λ) of the dark signal, and the value corresponding to the spectrum waveform of the measurement reflected light from the reference measurement object given by the denominator of formula (6), the spectroscopic reflectivity data Rsig (λ) of the measurement object is calculated (reflectivity calculation step S94). The calculation of the spectroscopic reflectivity data Rsig (λ) is executed in the reflectivity calculation unit 93.

[Mathematical formula 6]

$$Rsig(\lambda) = \frac{(S'sig(\lambda) - D'sig(\lambda))}{(S'ref(\lambda) - D'ref(\lambda)) \times K(\lambda)} \quad (6)$$

The spectroscopic reflectivity data Rsig (λ) measured by the reflectivity measuring device 1B in this embodiment is output to the membrane thickness calculation unit 19. In the membrane thickness calculation unit 19, the membrane thickness of the measurement object is calculated based on the spectroscopic reflectivity data Rsig (λ) (S96).

With the reflectivity measuring device 1 and the reflectivity measuring method according to this embodiment, a value corresponding to the spectrum waveform S'sig (λ) of the measurement reflected light from the reference measurement object can be calculated for each measurement from the spectrum waveform S'ref (λ) of the measurement irradiation light with which the measurement object is irradiated and the conversion coefficient K (λ) recorded in the coefficient recording unit 92, in a similar manner to the first embodiment described above. Accordingly, even in the case where the spectrum waveform S'ref (λ) of the measurement irradiation light fluctuates, it is possible to cancel the influence of fluctuation in the spectrum waveform S'ref (λ) of the measurement irradiation light included in the spectrum waveform S'sig (λ) of the measurement reflected light from the measurement object. Thus, the spectroscopic reflectivity data Rsig (λ) of the measurement object can be accurately measured.

With the reflectivity measuring device 1B according to this embodiment, it is possible for the spectroscopic detection unit 80B to be configured by one photodetector 83. With this configuration, the reflectivity measuring device 1B can be simplified in configuration and reduced in size. Further, since it is possible to reduce members and manufacturing steps necessary for manufacture by simplifying the configuration of the reflectivity measuring device 1B, manufacturing cost of the reflectivity measuring device 1B can be reduced.

Fourth Embodiment

Subsequently, a fourth embodiment that is a modified example of the third embodiment will be described. The difference of the third embodiment described above and this embodiment is in a method of calculating the conversion coefficient K (λ). In the third embodiment, the conversion coefficient K (λ) is calculated by controlling the measurement light source 30. However, in this embodiment, the conversion coefficient K (λ) is calculated by controlling the optical waveguide selecting device 40 in a state where the measurement light source 30 is turned on. Note that the reflectivity measuring device 1B used in this embodiment includes a configuration similar to the reflectivity measuring device 1B used in the third embodiment. Also, a step shown in FIG. 17 of calculating the membrane thickness or the like of a measurement object based on the spectroscopic reflectivity data Rsig (λ) is similar to the step in the third embodiment.

Figure 18:
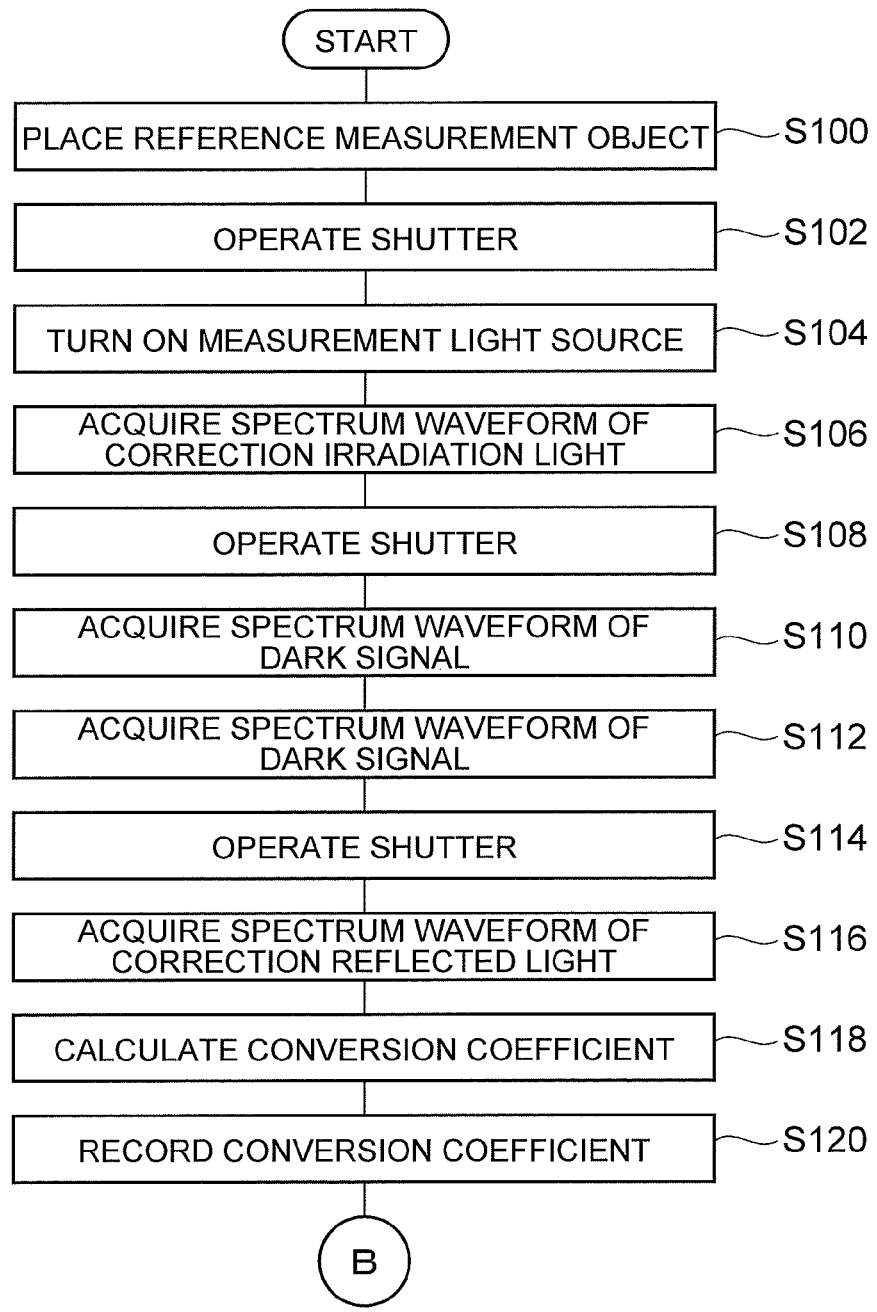
FIG. 18 is a flowchart showing the procedure of calculating a conversion coefficient according to a fourth embodiment.

The step of calculating the conversion coefficient K (λ) shown in FIG. 18 will be described. As the method of calculating the conversion coefficient K (λ) in this embodiment, a method of calculating the conversion coefficient K (λ) by controlling the optical waveguide selecting device 40 to acquire the spectrum waveform of a dark signal will be described.

A reference measurement object of which the spectroscopic reflectivity data Rref (λ) is known is placed in the sample measurement unit 11 (S100). Next, the optical waveguide selecting device 40 is controlled to operate the shutter 41 such that irradiation of the irradiation light L1 to the irradiation light reception surface 61 is blocked and only the reference light reception surface 51 is irradiated with the irradiation light L1 (S 102). Next, the measurement light source 30 is turned on (S 104). Herein, in the step of calculating the conversion coefficient K (λ), the irradiation light L1 from the measurement light source 30 is referred to as correction irradiation light.

The correction irradiation light with which the reference light reception surface 51 is irradiated is guided to the third detection unit 85 by the reference optical waveguide 50. The correction irradiation light guided to the third detection unit 85 is dispersed into wavelength components by the spectroscopic optical system 82. Then, the spectrum waveform Sref (λ) of the correction irradiation light is acquired by the photodetector 83 (correction irradiation light detection step S106). At this time, amount of time for which the spectrum waveform Sref (λ) of the correction irradiation light is acquired is set to arbitrary time length.

Next, the optical waveguide selecting device 40 is controlled to operate the shutter 41 such that the reference light reception surface 51 and the measurement light source 61 are not irradiated with the correction irradiation light (S108). Then, the spectrum waveform Dref (λ) of the dark signal output from the third detection unit 85 is acquired (S 110). Amount of time for which the spectrum waveform Dref (λ) of the dark signal is acquired is set to be about the same as the amount of time for which the spectrum waveform Sref (λ) of the correction irradiation light is acquired. Further, the spectrum waveform Dsig (λ) of the dark signal output from the third detection unit 85 is acquired (S112). Note that Dref (λ) and Dsig (λ) may be measured simultaneously. Next, the optical waveguide selecting device 40 is controlled to operate the shutter 41 such that the irradiation light reception surface 61 is irradiated with the correction irradiation light. The correction irradiation light with which the irradiation light reception surface 61 is irradiated is supplied to the reference measurement object via the first measurement optical waveguide 60 and the measurement optical system 14 (correction irradiation light supply step S114).

The correction irradiation light supplied to the reference measurement object is reflected on the surface of the reference measurement object and becomes the reflected light L2. Herein, the reflected light L2 is referred to as correction reflected light. The correction reflected light is guided to the third detection unit 85 by the measurement optical system 14 and the second measurement optical waveguide 70. The correction reflected light guided to the third detection unit 85 is dispersed into wavelength components in the spectroscopic optical system 82. Then, the spectrum waveform Ssig (λ) of the correction reflected light is acquired by the photodetector 83 (first reflected light detection step S116). At this time, amount of time for which the spectrum waveform of the correction reflected light is acquired is set to arbitrary time length.

Formula (7) shown below is a formula for calculating the conversion coefficient K (λ). Based on the spectroscopic reflectivity data Rref (λ) of the reference measurement object, the spectrum waveform Sref (λ) of the correction irradiation light, the spectrum waveform Ssig (λ) of the correction reflected light, and the spectrum waveforms Dref (λ) and Dsig (λ) of the dark signals output from the third detection unit 85, the conversion coefficient K (λ) is calculated (coefficient calculation step S118). The calculation of the conversion coefficient K (λ) is executed in the coefficient calculation unit 91. The conversion coefficient K (λ) is recorded in the coefficient recording unit 92 (S120). Note that it suffices to carry out the step of calculating the conversion coefficient K (λ) described above at the time of a shipping inspection or in a routine maintenance work.

[Mathematical formula 7]

$$K(\lambda) = \frac{(Ssig(\lambda) - Dsig(\lambda))}{(Sref(\lambda) - Dref(\lambda)) \times Rref(\lambda)} \quad (7)$$

With the above-described method of calculating the conversion coefficient K (λ) by controlling the optical waveguide selecting device 40, it is possible to acquire the spectroscopic reflectivity data Rref (λ) of the reference measurement object, the spectroscopic reflectivity data Sref (λ) of the correction irradiation light, the spectrum waveform Ssig (λ) of the correction reflected light, and the spectrum waveforms Dref (λ) and Dsig (λ) of the dark signals output from the third detection unit 85 in a state where the measurement light source 30 is continuously turned on. Therefore, the conversion coefficient K (λ) can be calculated in the state where the measurement light source 30 is continuously turned on. Thus, it is possible to maintain the state where the measurement light source 30 is turned on during measurement, and the spectrum waveform of the irradiation light L1 from the measurement light source 30 can be stabilized.

Figure 19:
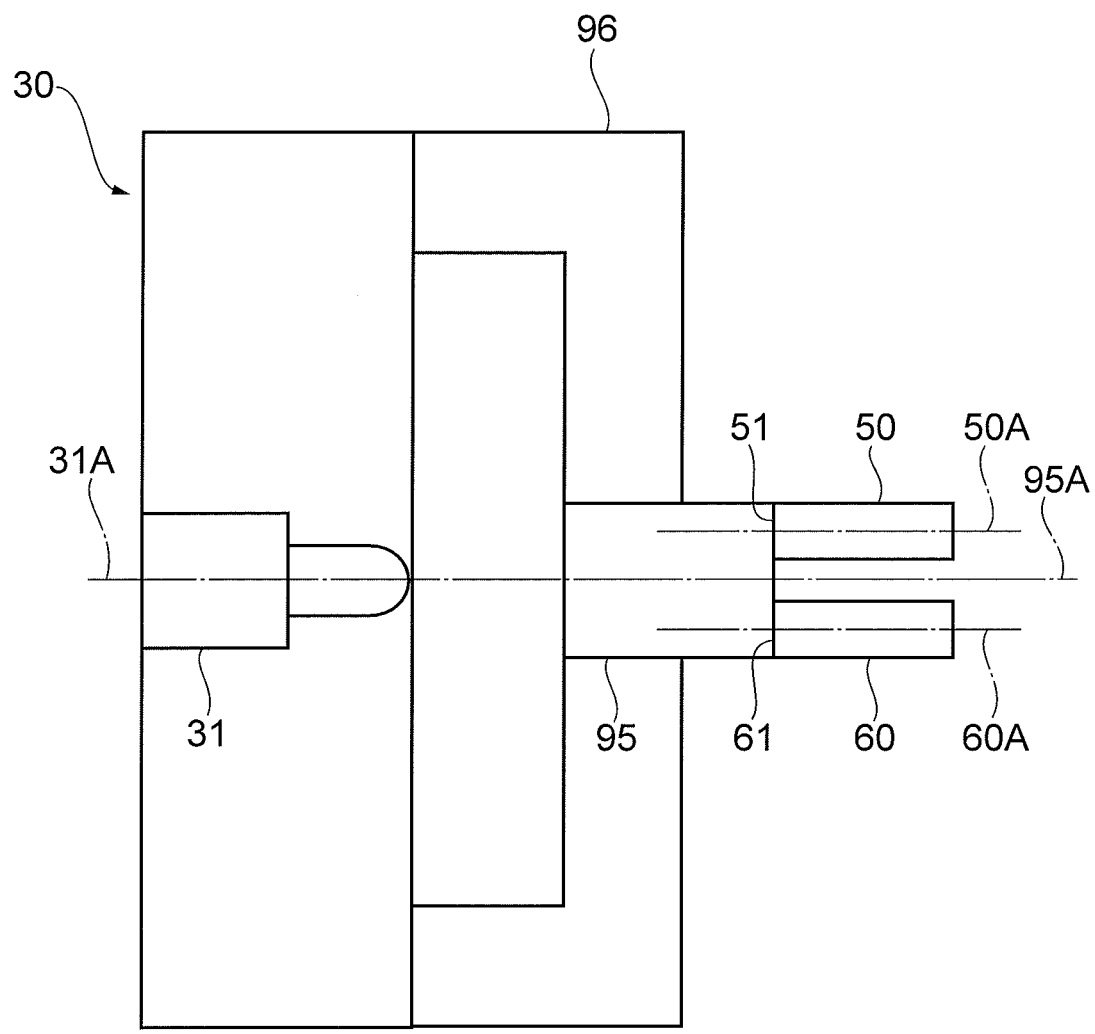
FIG. 19 is a configuration diagram showing a modified example of the configuration of the measurement light source, the reference optical waveguide, and the first measurement optical waveguide.

The reflectivity measuring device and the reflectivity measuring method according to the present invention are not limited to the embodiments described above, and various modifications are possible. For example, in the first embodiment and the second embodiment described above, the reference optical waveguide 50 and the first measurement optical waveguide 60 may be optically coupled with the measurement light source 30 via a bundle fiber 95, as shown in FIG. 19. The reference optical waveguide 50 and the first measurement optical waveguide 60 are optically coupled to one end of the bundle fiber 95 via the reference light reception surface 51 and the irradiation light reception surface 61. The central axis 50A of the reference optical waveguide 50 and the central axis 60A of the first measurement optical waveguide 60 are arranged to be line symmetrical with respect to a central axis 95A of the bundle fiber 95. The bundle fiber 95 is held by an optical waveguide holding unit 96 and is optically coupled such that an axis passing through the center of the white LED 31 and the central axis 95A of the bundle fiber 95 approximately coincide.

With the reflectivity measuring device 1 including the configuration shown in FIG. 19, a position adjustment of the axis 31A passing through the white LED 31 and the central axis 50A of the reference optical waveguide 50 as well as the central axis 60A of the first measurement optical waveguide 60 can be performed easily.

In the case where the optical waveguide is branched by the bundle fiber 95, an ideal random arrangement of fibers configuring the bundle fiber 95 is desirable. In the case where the ideal random arrangement of the fibers configuring the bundle fiber 95 is difficult due to a manufacture problem, the reflectivity measuring device 1 can also be configured without using the bundle fiber 95. With a configuration not using the bundle fiber 95, the manufacturing cost of the reflectivity measuring device 1 can be reduced.

In the case where it is necessary to adjust the measure of the light amount of the irradiation light L1 that enters the reference optical waveguide 50 and the irradiation light L1 that enters the first measurement optical waveguide 60, the reflectivity measuring device 1 can also be configured without using the bundle fiber 95. With a configuration not using the bundle fiber 95, the measure of the light amount of the irradiation light L1 that enters the reference optical waveguide 50 and the irradiation light L1 that enters the first measurement optical waveguide 60 can be adjusted.

Figure 20:
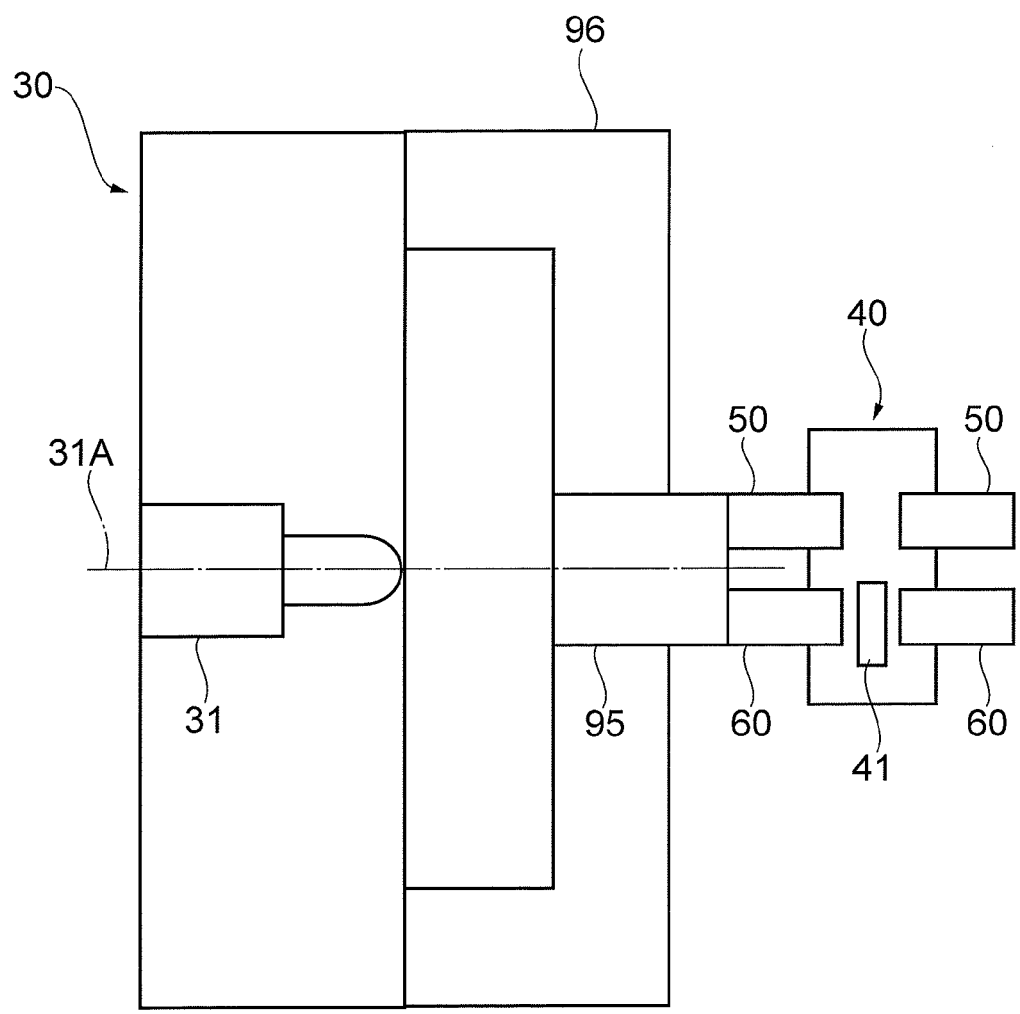
FIG. 20 is a configuration diagram showing another modified example of the configuration of the measurement light source, the reference optical waveguide, and the first measurement optical waveguide.

Further, FIG. 20 shows the configuration of another modified example of the reflectivity measuring device 1 including the bundle fiber 95. The difference from the modified example in FIG. 19 is that the optical waveguide selecting device 40 is included. By including the optical waveguide selecting device 40, at least one of the reference optical waveguide 50 and the first measurement optical waveguide 60 can be selectively irradiated with the irradiation light L1 from the white LED 31. Also, both the reference optical waveguide 50 and the first measurement optical waveguide 60 can be kept from being irradiated.

In the reflectivity measuring device 1 including the configuration shown in FIG. 20, there are cases where the configuration of the reflectivity measuring device 1 is complicated. In the case where the reflectivity measuring device 1 with a simple configuration is desired, the reflectivity measuring device 1 can also be configured without using the bundle fiber 95. With a configuration not using the bundle fiber 95, the configuration including the measurement light source 30 and the optical waveguide selecting device 40 can be simplified. Further, with the simple configuration, the measurement light source 30 and the optical waveguide selecting device 40 can easily be integrated. Further, the configuration including the measurement light source 30 and the optical waveguide selecting device 40 can easily be reduced in size.

In the first embodiment to the fourth embodiment described above, the reference optical waveguide 50 and the first measurement optical waveguide 60 are arranged such that the central axis 50A of the reference optical waveguide 50 and the central axis 60A of the first measurement optical waveguide 60 are line symmetrical with respect to the axis 31A passing through the white LED 31, but may be arranged such that the white LED 31 and the first measurement optical waveguide 60 are opposed, as shown in FIG. 21(*a*). With this, the light amount of the irradiation light L1 supplied to the sample 12 can be increased. Thus, even in the case where the irradiation light L1 or the reflected light L2 has attenuated due to passing through the optical waveguide or the like, the light amount necessary for accurately measuring the spectroscopic reflectivity data Rsig (λ) can be ensured. Also, as in FIG. 21(*b*), the optical waveguide selecting device 40 may be included therein.

Figure 22:
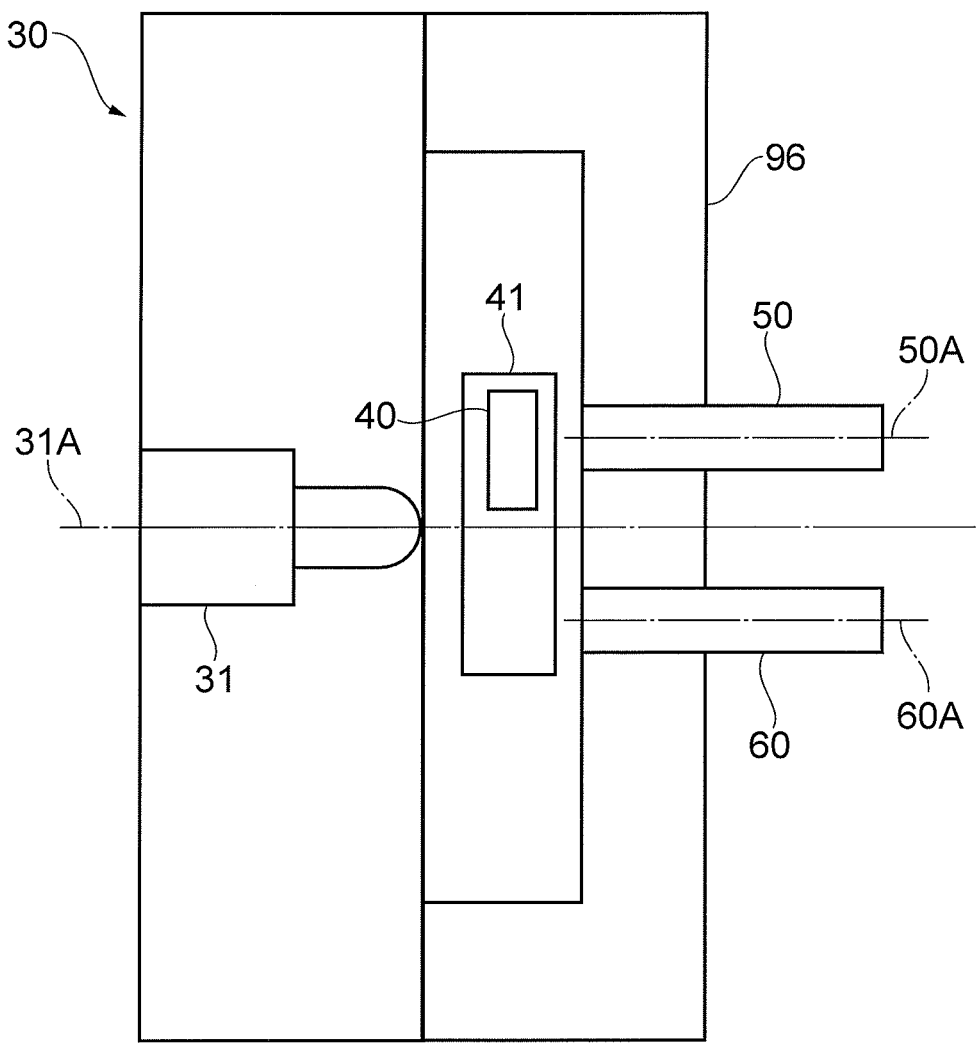
FIG. 22 is a configuration diagram showing still another modified example of the configuration of the measurement light source, the reference optical waveguide, and the first measurement optical waveguide.

The optical waveguide selecting device 40 is not included in the reflectivity measuring device 1 shown in the first embodiment and the reflectivity measuring device 1A shown in the second embodiment described above, but the optical waveguide selecting device 40 may be included therein as shown in FIG. 22.

In the first embodiment to the fourth embodiment described above, it is necessary to acquire, for each measurement, the spectrum waveform Sref (λ) of the irradiation light L1 and the Dsig (λ) and Dref (λ) that are correction data for dark subtraction correction. The reflectivity measuring device and the reflectivity measuring method according to the present invention are not limited as such. For example, if the fluctuation in the spectrum waveform Sref (λ) of the irradiation light L1 and the spectrum waveforms Dsig (λ) and Dref (λ) within a continuous measurement time is to a degree that does not influence the measurement result, the acquisition of the spectrum waveform Sref (λ) of the irradiation light L1 and the spectrum waveforms Dsig (λ) and Dref (λ) of the dark signals may be carried out only once immediately after start of measurement to store the data and the stored data may be used thereafter. Accordingly, take time can be shortened.

In the first embodiment to fourth embodiment described above, the reflectivity measuring device 1 is used in the membrane thickness measuring device 10 that calculates the membrane thickness based on the calculated value of the spectroscopic reflectivity data. The reflectivity measuring device 1 according to the present invention is not limited as such and may be used in a color measuring device that measures color, a reflectivity measuring device that measures reflectivity, or a transmittance measuring device that measures transmittance based on the calculated value of the spectroscopic reflectivity data.

In the first embodiment, the third embodiment, and the fourth embodiment described above, the conversion coefficient K (λ) is calculated using formula (8) shown below, and the spectroscopic reflectivity data Rsig (λ) is further calculated using formula (9). The reflectivity measuring device 1 according to the present invention is not limited as such and may calculate the conversion coefficient K (λ) using formula (10) shown below and further calculate the spectroscopic reflectivity data Rsig (λ) using formula (11).

[Mathematical formula 8]

$$K(\lambda) = \frac{(Ssig(\lambda) - Dsig(\lambda))}{(Sref(\lambda) - Dref(\lambda)) \times Rref(\lambda)} \quad (8)$$

[Mathematical formula 9]

$$Rsig(\lambda) = \frac{(S'sig(\lambda) - D'sig(\lambda))}{(S'ref(\lambda) - D'ref(\lambda)) \times K(\lambda)} \quad (9)$$

[Mathematical formula 10]

$$K(\lambda) = \frac{(Ssig(\lambda) - Dsig(\lambda))}{(Sref(\lambda) - Dref(\lambda))} \quad (10)$$

[Mathematical formula 11]

$$Rsig(\lambda) = \frac{(S'sig(\lambda) - D'sig(\lambda)) \times Rref(\lambda)}{(S'ref(\lambda) - D'ref(\lambda)) \times K(\lambda)} \quad (11)$$

INDUSTRIAL APPLICABILITY

It is possible to utilize the present invention as a reflectivity measuring device as well as a reflectivity measuring method that can accurately measure the each wavelength's reflectivity of a measurement object and a membrane thickness measuring device as well as a membrane thickness measuring method that can accurately measure the membrane thickness of a measurement object.

REFERENCE SIGNS LIST

1 . . . Reflectivity measuring device, 30 . . . Measurement light source, 80 . . . Spectroscopic detection unit, 92 . . . Coefficient recording unit, 93 . . . Reflectivity calculation unit, L1 . . . Irradiation light, L2 . . . Reflected light, K (λ) . . . Conversion coefficient

The invention claimed is:

1. A reflectivity measuring device comprising:
a measurement light source configured to supply irradiation light to a measurement object;
a spectroscopic detection unit configured to detect, at multi-wavelength, intensity of the irradiation light and intensity of reflected light from the measurement object;
a coefficient recording unit configured to record a conversion coefficient to convert a detected value of each wavelength's intensity of the irradiation light into a value corresponding to each wavelength's intensity of reflected light from a reference measurement object;
a reflectivity calculation unit configured to calculate each wavelength's reflectivity of the measurement object based on the value corresponding to the each wavelength's intensity of the reflected light from the reference measurement object obtained from the detected value of the each wavelength's intensity of the irradiation light and the conversion coefficient;
a reference optical waveguide configured to have at one end a reference light reception surface irradiated with the irradiation light from the measurement light source and of which another end is optically coupled to the spectroscopic detection unit;
a first measurement optical waveguide configured to have at one end an irradiation light reception surface irradiated with the irradiation light from the measurement light source and at another end an irradiation light supply surface that supplies the irradiation light to the measurement object; and
a second measurement optical waveguide configured to have at one end a reflected light reception surface to receive the reflected light from the measurement object and of which another end is optically coupled to the spectroscopic detection unit.

2. The reflectivity measuring device according to claim 1, wherein
the measurement light source is a phosphor-based white light-emitting diode that supplies irradiation light including excitation light and fluorescence generated by the excitation light.

3. The reflectivity measuring device according to claim 1, wherein
the spectroscopic detection unit includes a first detection unit that detects intensity of the irradiation light at multi-wavelength and a second detection unit that detects intensity of the reflected light from the measurement object at multi-wavelength, and
the other end of the reference optical waveguide is optically coupled to the first detection unit and the other end of the second measurement optical waveguide is optically coupled to the second detection unit.

4. The reflectivity measuring device according to claim 1, further comprising optical waveguide selecting device configured to cause the irradiation light from the measurement light source to be selectively incident upon one of the reference light reception surface and the irradiation light reception surface, wherein
the spectroscopic detection unit includes a third detection unit that detects intensity of the irradiation light at multi-wavelength and detects intensity of the reflected light at multi-wavelength, and the other end of the reference optical waveguide and the other end of the second measurement optical waveguide are optically coupled to the third detection unit.

5. The reflectivity measuring device according to claim 1, wherein the light amount of the irradiation light with which the irradiation light reception surface is irradiated is larger than the light amount of the irradiation light with which the reference light reception surface is irradiated.

6. The reflectivity measuring device according to claim 5, wherein the first measurement optical waveguide is arranged such that the irradiation light reception surface and the measurement light source are opposed.

7. The reflectivity measuring device according to claim 1, wherein the first measurement optical waveguide and the reference optical waveguide are arranged such that a central axis of the first measurement optical waveguide and a central axis of the reference optical waveguide are line symmetrical with respect to an axis passing through the measurement light source.

8. A membrane thickness measuring device comprising a reflectivity measuring device, wherein
the reflectivity measuring device comprises:
a measurement light source configured to supply irradiation light to a measurement object;
a spectroscopic detection unit configured to detect, at multi-wavelength, intensity of the irradiation light and intensity of reflected light from the measurement object;
a coefficient recording unit configured to record a conversion coefficient to convert a detected value of each wavelength's intensity of the irradiation light into a value corresponding to each wavelength's intensity of reflected light from a reference measurement object;
a reflectivity calculation unit configured to calculate each wavelength's reflectivity of the measurement object based on the value corresponding to the each wavelength's intensity of the reflected light from the reference measurement object obtained from the detected value of the each wavelength's intensity of the irradiation light and the conversion coefficient;
a reference optical waveguide configured to have at one end a reference light reception surface irradiated with the irradiation light from the measurement light source and of which another end is optically coupled to the spectroscopic detection unit;
a first measurement optical waveguide configured to have at one end an irradiation light reception surface irradiated with the irradiation light from the measurement light source and at another end an irradiation light supply surface that supplies the irradiation light to the measurement object; and
a second measurement optical waveguide configured to have at one end a reflected light reception surface to receive the reflected light from the measurement object and of which another end is optically coupled to the spectroscopic detection unit.

9. A reflectivity measuring method comprising:
first detecting, at multi-wavelength, intensity of correction irradiation light supplied to a reference measurement object;
first supplying the correction irradiation light from a measurement light source to the reference measurement object;
second detecting, at multi-wavelength, intensity of reflected light of the correction irradiation light from the reference measurement object;
first calculating a conversion coefficient configured to convert a detected value of each wavelength's intensity of measurement irradiation light supplied to a measurement object into a value corresponding to each wavelength's intensity of reflected light of the measurement irradiation light from the reference measurement object based on a detected value of each wavelength's intensity of the correction irradiation light obtained by the first detecting step and a detected value of each wavelength's intensity of the reflected light of the correction irradiation light obtained by the second detecting step;
placing the measurement object;
third detecting, at multi-wavelength, intensity of the measurement irradiation light including excitation light and fluorescence generated by the excitation light;
second supplying the measurement irradiation light from the measurement light source to the measurement object;
fourth detecting, at multi-wavelength, intensity of reflected light of the measurement irradiation light from the measurement object; and
second calculating each wavelength's reflectivity of the measurement object based on the value corresponding to each wavelength's intensity of the reflected light of the measurement irradiation light from the reference measurement object obtained from a detected value of each wavelength's intensity of the measurement irradiation light obtained by the third detecting step and the conversion coefficient and a detected value of each wavelength's intensity of the reflected light of the measurement irradiation light from the measurement object obtained by the fourth detecting step.

10. A membrane thickness measuring method comprising the reflectivity measuring method according to claim 9, wherein membrane thickness of the measurement object is calculated based on the each wavelength's reflectivity obtained through the reflectivity measuring method.

* * * * *